United States Patent [19]  
Cantatore et al.

[11] Patent Number: 4,803,234  
[45] Date of Patent: Feb. 7, 1989

[54] PIPERIDINE COMPOUNDS AND THEIR USE AS ANTI-OXIDATIVE, LIGHT OR THERMAL INDUCED DEGRADATION AGENTS

[75] Inventors: Giuseppe Cantatore, Bitonto; Valerio Borzatta, Bologna, both of Italy

[73] Assignee: Ciba-Geigy Corporation, Ardsley, N.Y.

[21] Appl. No.: 8,220

[22] Filed: Jan. 29, 1987

[30] Foreign Application Priority Data

Jan. 30, 1986 [IT] Italy ............................ 19230 A/86

[51] Int. Cl.⁴ ..................... C08J 5/34; C09K 15/16; C07D 251/40
[52] U.S. Cl. ............................. 524/100; 252/401; 252/403; 544/180; 544/194; 544/214; 544/215; 546/22; 546/24; 546/186; 546/244
[58] Field of Search ................ 252/401; 524/100; 544/180, 194, 214, 215

[56] References Cited

U.S. PATENT DOCUMENTS 4,021,471  5/1977  Virgilio et al. ............ 260/45.8 N

FOREIGN PATENT DOCUMENTS 6084258  5/1985  Japan ........................ 260/45.8 N
2176482 12/1986  United Kingdom ....... 260/45.8 N

OTHER PUBLICATIONS

Hack's Chemical Dictionary, pp. 16 and 86.

Primary Examiner—Mary C. Lee  
Assistant Examiner—J. Richter  
Attorney, Agent, or Firm—Luther A. R. Hall

[57] ABSTRACT

Compounds of formula (I)

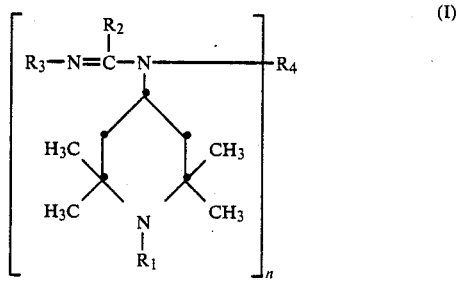

in which $R_1$ is hydrogen, O·, CN, NO, cyanomethyl, $C_1$-$C_{12}$-alkyl, $C_3$-$C_{12}$-alkenyl or $C_3$-$C_{12}$-alkynyl subject to the proviso that the carbon atom attached to the nitrogen atom is a primary carbon atom, $C_7$-$C_{12}$-aralkyl, $C_1$-$C_{12}$-acyl, 2,3-epoxypropyl, OH-monosubstituted $C_2$-$C_6$-alkyl or 2,3-dihydroxypropyl, $R_2$ is hydrogen, $C_1$-$C_{18}$-alkyl, $C_5$-$C_{18}$-cycloalkyl, $C_6$-$C{hd 18}$-aryl or $C_7$-$C_{18}$-aralkyl, $R_3$ is $C_6$-$C_{18}$-aryl or a group of the formula (II)

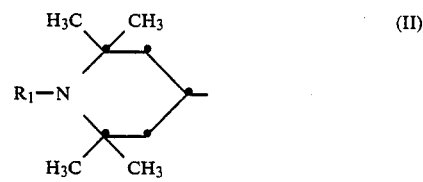

in which $R_1$ is as defined above, n is an integer from 1 to 4 and $R_4$ is an organic or inorganic radical of a valency equal to n are useful for stabilizing organic material against oxidative, thermal and/or light induced degradation.

18 Claims, No Drawings

PIPERIDINE COMPOUNDS AND THEIR USE AS ANTI-OXIDATIVE, LIGHT OR THERMAL INDUCED DEGRADATION AGENTS

The present invention relates to novel piperidine compounds, the use thereof and to the organic material stabilized with the aid of said compounds against thermal, oxidative and/or light induced degradation.

It is known that synthethic polymers undergo progressive changes in their physical properties, such as loss of mechanical strength and colour changes, when they are exposed to sunlight or other sources of ultraviolet light. To retard the deleterious effect of sunlight on synthetic polymers, it has been proposed to use various additives having light-stabilizing properties.

FR No. 2 268 011 describes substituted N,N'-diphenylformamidine compounds and the use thereof as light stabilizers. JP No. 85-84258 discloses a process for the preparation of substituted N,N'-formamidine derivatives.

The present invention relates to novel piperidine compounds of the formula (I)

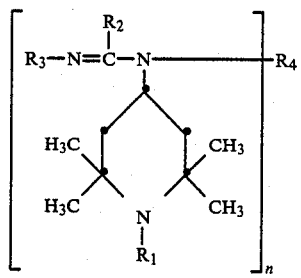

in which $R_1$ is hydrogen, O·, CN, NO, cyanomethyl, $C_1$–$C_{12}$-alkyl, $C_3$–$C_{12}$-alkenyl or $C_3$–$C_{12}$-alkynyl subject to the proviso that the carbon atom attached to the nitrogen atom is a primary carbon atom, $C_7$–$C_{12}$-aralkyl, $C_1$–$C_{12}$-acyl, 2,3-epoxypropyl, OH-monosubstituted $C_2$–$C_6$-alkyl or 2,3-dihydroxypropyl, $R_2$ is hydrogen, $C_1$–$C_{18}$-alkyl, $C_5$–$C_{18}$-cycloalkyl, $C_6$–$C_{18}$-aryl or $C_7$–$C_{18}$-aralkyl, $R_3$ is $C_6$–$C_{18}$-aryl or a group of the formula (II)

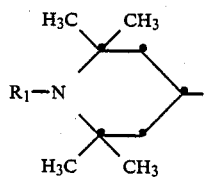

in which $R_1$ is as defined above, n is an integer from 1 to 4 and $R_4$ is an organic or inorganic radical of a valency equal to n.

If n is 1, $R_4$ is preferably selected from the group consisting of hydrogen, CN,

—$COR_5$, —$COOR_6$, —CO—$R_7$—$COOR_8$,

—CO—$R_7$—CON(—$R_{10}$)—$R_9$, —CON(—$R_{10}$)—$R_9$, —CSN(—$R_{10}$)—$R_9$, —$SO_2R_{11}$,

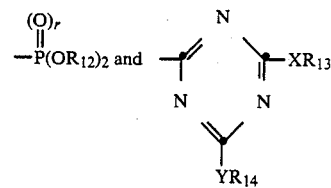

in which $R_5$ is hydrogen, $C_1$–$C_{18}$-alkyl, $C_5$–$C_{18}$-cycloalkyl, $C_2$–$C_{18}$-alkenyl, $C_6$–$C_{18}$-aryl, $C_7$–$C_{18}$-aralkyl or $C_1$–$C_{10}$-alkyl substituted by $C_1$–$C_{18}$-alkoxy, by $C_2$–$C_{18}$-dialkylamino or by a group of the formula (III)

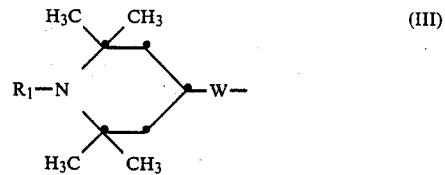

where $R_1$ is as defined above and W is —O— or

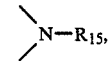

where $R_{15}$ is hydrogen, $C_1$–$C_{18}$-alkyl, $C_5$–$C_{18}$-cycloalkyl, $C_3$–$C_{18}$-alkenyl, $C_6$–$C_{18}$-aryl, $C_7$–$C_{18}$-aralkyl or a group of the formula (II), $R_6$ is $C_1$–$C_{18}$-alkyl, $C_2$–$C_6$-alkyl substituted by OH, by $C_1$–$C_{18}$-alkoxy or by $C_2$–$C_{18}$-dialkylamino, $C_5$–$C_{18}$-cycloalkyl, $C_3$–$C_{18}$-alkenyl, $C_6$–$C_{18}$-aryl, $C_7$–$C_{18}$-aralkyl or a group of the formula (II), $R_7$ is a direct bond, $C_1$–$C_{18}$-alkylene, $C_2$–$C_{20}$-alkylidene, $C_7$–$C_{20}$-aralkylidene, $C_6$–$C_{10}$-cycloalkylene, $C_2$–$C_{18}$-alkenylene or $C_6$–$C_{10}$-arylene, $R_8$ is as defined for $R_6$ or is hydrogen or an alkali metal, $R_9$ and $R_{10}$, which are identical or different, are as defined for $R_{15}$, or $R_9$ and $R_{10}$, together with the nitrogen atom to which they are bonded, form part of a 5-membered to 7-membered heterocyclic ring, $R_{11}$ is $C_1$–$C_{12}$-alkyl or $C_6$–$C_{12}$-aryl, r is 0 or 1, $R_{12}$ is $C_1$–$C_{12}$-alkyl or a group of the formula (II), or the two groups $R_{12}$ together are $C_2$–$C_{12}$-alkylene or $C_6$–$C_{28}$-arylene and together with the phosphorus atom and the two oxygen atoms form a 5-membered to 7-membered ring, $R_{13}$ and $R_{14}$, which can be identical or different, are as defined for $R_6$ or are hydrogen, and X and Y, which can be identical or different, are a direct bond, —O— or

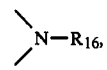

where $R_{16}$ is as defined for $R_{15}$ or is OH-monosubstituted $C_2$–$C_6$-alkyl, or the groups $R_{13}X$— and $R_{14}Y$—, which can be identical or different, are a 5-membered to 7-membered heterocyclic group.

If n is 2, $R_4$ is preferably selected from the group consisting of

—CO—, —$SO_2$—, —COO—$R_{17}$—OOC—,
—COCOO—$R_{17}$—OOCCO—, —CO—$R_{18}$—CO—,

-continued

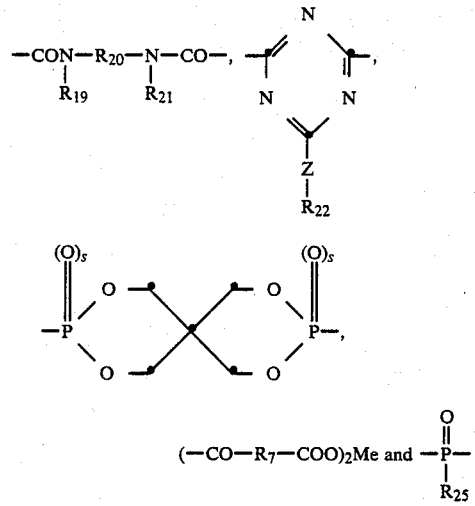

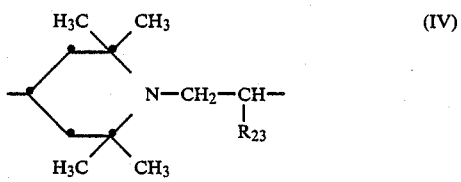

$(-CO-R_7-COO)_2Me$ and 

in which $R_{17}$ is $C_2$–$C_{18}$-alkylene, $C_4$–$C_{12}$-alkylene substituted in the chain by 1 or 2 oxygen atoms, $C_6$–$C_{18}$-cycloalkylene, $C_4$–$C_8$-alkenylene, $C_6$–$C_{18}$-arylene, $C_8$–$C_{12}$-aralkylene or a group of the formula (IV)

$$\text{(IV)}$$

where $R_{23}$ is hydrogen, $C_1$–$C_4$-alkyl or phenyl, $R_{18}$ is a direct bond, $C_1$–$C_{18}$-alkylene, $C_2$–$C_{20}$-alkylidene, $C_7$–$C_{20}$-aralkylidene, $C_6$–$C_{10}$-cycloalkylene, $C_6$–$C_{10}$-arylene, $C_2$–$C_{12}$-alkylene substituted in the chain by 1 or 2 oxygen atoms or by 1 or 2 groups $$\diagdown\!\!\!N\!-\!R_{24},\!\!\diagup$$

where $R_{24}$ is as defined for $R_{15}$, $R_{19}$ and $R_{21}$, which can be identical or different, are as defined for $R_{15}$, $R_{20}$ is $C_2$–$C_{18}$-alkylene, $C_6$–$C_{18}$-cycloalkylene, $C_6$–$C_{18}$-arylene or $C_8$–$C_{12}$-aralkylene, $R_{22}$ is as defined for $R_{13}$ and $R_{14}$, Z is as defined for X and Y, or $-ZR_{33}$ is a 5-membered to 7-membered heterocyclic group or halogen, $R_{25}$ is $C_1$–$C_4$-alkyl, s is 0 or 1, $R_7$ is as defined above and Me is Ba, Ca, Co", Mg, Mn", Ni", Sn" or Zn.

If n is 3, $R_4$ is preferably selected from the group consisting of aliphatic $C_4$–$C_{18}$-triacyl, aliphatic $C_6$–$C_{18}$-triacyl substituted by a nitrogen atom, aromatic or heterocyclic triacyl having up to 18 carbon atoms, substituted aliphatic, aromatic or heterocyclic tricarbamoyl having up to 24 carbon atoms, a 1,3,5-triazine-2,4,6-triyl group, a ≡P group, a ≡PO group and a group $(-CO-R_7-COO)_3Al$ with $R_7$ as defined above.

If n is 4, $R_4$ is preferably selected from the group consisting of aliphatic $C_6$–$C_{18}$-tetraacyl, aliphatic $C_{10}$–$C_{18}$-tetraacyl substituted by two nitrogen atoms, aromatic $C_{10}$–$C_{18}$-tetraacyl, cycloaliphatic $C_{10}$–$C_{22}$-tetraacyl and a group $(-CO-R_7-COO)_4Sn^{IV}$, where $R_7$ is as defined above.

$R_1$, $R_{11}$ and $R_{12}$ as $C_1$–$C_{12}$-alkyl are for example methyl, ethyl, propyl, isopropyl, butyl, isobutyl, t-butyl, pentyl, hexyl, heptyl, octyl, 2-ethylhexyl, decyl or dodecyl. $C_1$–$C_4$-alkyl which may be straight or branched is preferred. $R^1$ as methyl is especially preferred.

$R_1$ as $C_3$–$C_{12}$-alkenyl is for example allyl, 2-methallyl, 2-butenyl, 2-hexenyl or 10-undecenyl. Allyl is especially preferred.

$R_1$ as $C_3$–$C_{12}$-alkynyl may be preferably propargyl.

$R_1$ as $C_7$–$C_{12}$-aralkyl is for example benzyl, methylbenzyl, t-butylbenzyl or hydroxybenzyl. $C_7$–$C_{10}$-phenylalkyl unsubstituted or substituted at the phenyl ring by alkyl and/or by OH is preferred. Benzyl and benzyl substituted by $C_1$–$C_4$-alkyl and/or by OH are especially preferred.

$R_1$ as $C_1$–$C_{12}$-acyl may be an aliphatic or aromatic $C_1$–$C_{12}$-acyl group. $C_1$–$C_{12}$-alkanoyl, $C_3$–$C_{12}$-alkenoyl, $C_3$–$C_{12}$-alkynoyl, benzoyl and benzoyl substituted by $C_1$–$C_4$-alkyl and/or by OH are preferred. Examples are formyl, acetyl, propionyl, butyryl, caproyl, capryloyl, caprinoyl, lauroyl, benzoyl, acryloyl, methacryloyl and crotonoyl.

$R_1$, $R_6$, $R_{13}$, $R_{14}$, $R_{16}$ and $R_{22}$ as OH-monosubstituted $C_2$–$C_6$-alkyl are for example 2-hydroxyethyl, 2-hydroxypropyl or 3-hydroxypropyl.

$R_2$, $R_5$, $R_6$, $R_8$, $R_9$, $R_{10}$, $R_{13}$, $R_{14}$, $R_{15}$, $R_{16}$, $R_{19}$, $R_{21}$, $R_{22}$ and $R_{24}$ as $C_1$–$C_{18}$-alkyl are for example methyl, ethyl, propyl, isopropyl, butyl, isobutyl, 2-butyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, octadecyl or heptadecyl. $R_2$ is preferably $C_1$–$C_4$-alkyl, in particular methyl.

$R_2$, $R_5$, $R_6$, $R_8$, $R_9$, $R_{10}$, $R_{13}$, $R_{14}$, $R_{15}$, $R_{16}$, $R_{19}$, $R_{21}$, $R_{22}$ and $R_{24}$ as $C_5$–$C_{18}$-cycloalkyl are preferably a cycloalkyl group of the formula $-HC(CH_2)_a$ with a being an integer from 4 to 11. Said cycloalkyl group may optionally be substituted by $C_1$–$C_4$-alkyl. Examples are cyclopentyl, cyclohexyl, methylcyclohexyl, dimethylcyclohexyl, trimethylcyclohexyl, t-butylcyclohexyl, cyclooctyl and cyclododecyl. Cyclohexyl unsubstituted or substituted by $C_1$–$C_4$-alkyl is especially preferred.

$R_2$, $R_3$, $R_5$, $R_6$, $R_8$, $R_9$, $R_{10}$, $R_{13}$, $R_{14}$, $R_{15}$, $R_{16}$, $R_{19}$, $R_{21}$, $R_{22}$ and $R_{24}$ as $C_6$–$C_{18}$-aryl are for example phenyl or naphthyl which both may be substituted or unsubstituted.

$R_3$ as $C_6$–$C_{18}$-aryl may be preferably phenyl unsubstituted or substituted by $C_1$–$C_4$-alkyl, $C_1$–$C_4$-alkoxy, $C_2$–$C_4$-alkoxycarbonyl and/or OH, or may be phenyl substituted by 2,2,6,6-tetramethyl-4-piperidyloxycarbonyl or by 1,2,2,6,6-pentamethyl-4-piperidyloxycarbonyl. Preferred examples of $R_3$ are phenyl, methylphenyl, dimethylphenyl, trimethylphenyl, ethylphenyl, diethylphenyl, hydroxyphenyl, 3,5-di-t-butyl-4-hydroxyphenyl, methoxyphenyl, ethoxyphenyl, 4-ethoxycarbonylphenyl, 4-(2,2,6,6-tetramethyl-4-piperidyloxycarbonyl)phenyl and 4-(1,2,2,6,6-pentamethyl-4-piperidyloxycarbonyl)phenyl.

$R_2$, $R_5$, $R_9$, $R_{10}$, $R_{15}$, $R_{16}$, $R_{19}$, $R_{21}$ and $R_{24}$ as $C_6$–$C_{18}$-aryl may be preferably phenyl unsubstituted or substituted by $C_1$–$C_4$-alkyl, $C_1$–$C_4$-alkoxy and/or OH, or may be naphthyl unsubstituted or substituted by $C_1$–$C_4$-alkoxy. Preferred examples of $R_2$, $R_5$, $R_9$, $R_{10}$, $R_{15}$, $R_{16}$, $R_{19}$, $R_{21}$ and $R_{24}$ are phenyl, methylphenyl, dimethylphenyl, trimethylphenyl, ethylphenyl, t-butylphenyl, methoxyphenyl, ethoxyphenyl, hydroxyphenyl and 3,5-di-t-butyl-4-hydroxyphenyl with phenyl being especially preferred.

$R_6$, $R_8$, $R_{13}$, $R_{14}$ and $R_{22}$ as $C_6$–$C_{18}$-aryl may be preferably phenyl unsubstituted or substituted by $C_1$–$C_4$-alkyl and/or alkoxy, or may be naphthyl unsubstituted or substituted by $C_1$–$C_4$-alkoxy. Preferred examples of $R_6$, $R_8$, $R_{13}$, $R_{14}$ and $R_{22}$ are phenyl, methylphenyl, dimethylphenyl, trimethylphenyl, ethylphenyl, isopropylphenyl, t-butylphenyl, di-t-butylphenyl, 2,6-di-t-butyl-4-methylphenyl, methoxyphenyl and ethoxyphenyl.

$R_2$, $R_5$, $R_6$, $R_8$, $R_9$, $R_{10}$, $R_{13}$, $R_{14}$, $R_{15}$, $R_{16}$, $R_{19}$, $R_{21}$, $R_{22}$ and $R_{24}$ as $C_7$–$C_{18}$-aralkyl may be $C_7$–$C_{10}$-phenylalkyl unsubstituted or substituted at the phenyl ring by $C_1$–$C_4$-alkyl and/or OH. Examples are benzyl, methylbenzyl, hydroxybenzyl, 3,5-di-t-butyl-4-hydroxybenzyl and 2-(3,5-di-t-butyl-4-hydroxyphenyl)ethyl. Benzyl unsubstituted or substituted is preferred.

$R_5$ as $C_2$–$C_{18}$-alkenyl is for example vinyl, propenyl, allyl, butenyl, methylallyl, hexenyl, decenyl or heptadecenyl.

$R_5$ as $C_1$–$C_{10}$-alkyl which is substituted by $C_1$–$C_{18}$-alkoxy or $C_2$–$C_{18}$-dialkylamino is for example ethoxymethyl, butoxymethyl, octoxyethyl, 2-ethoxyethyl, 3-butoxyethyl, 3-methoxypropyl, 3-butoxypropyl, diethylaminomethyl, dibutylaminomethyl, 2-diethylaminoethyl, 2-dibutylaminoethyl or 3-diethylaminopropyl.

$R_6$, $R_8$, $R_{13}$, $R_{14}$ and $R_{22}$ as $C_2$–$C_6$-alkyl which is substituted by $C_1$–$C_{18}$-alkoxy or $C_2$–$C_{18}$-dialkylamino are for example 2-methoxyethyl, 2-ethoxyethyl, 2-butoxyethyl, 2-octoxyethyl, 2-ethoxypropyl, 3-butoxypropyl, 4-butoxybutyl, 2-diethylaminoethyl, 2-dibutylaminoethyl or 3-dibutylaminopropyl.

$R_6$, $R_8$, $R_9$, $R_{10}$, $R_{13}$, $R_{14}$, $R_{15}$, $R_{16}$, $R_{19}$, $R_{21}$, $R_{22}$ and $R_{24}$ as $C_3$–$C_{18}$-alkenyl are for example allyl, butenyl, methylallyl, hexenyl, decenyl, undecenyl or oleyl.

$R_7$ and $R_{18}$ as $C_1$–$C_{18}$-alkylene are for example methylene, ethylene, propylene, trimethylene, tetramethylene, pentamethylene, hexamethylene, heptamethylene, octamethylene, decamethylene or dodecamethylene. $C_1$–$C_6$-alkylene is preferred. Ethylene is especially preferred.

$R_7$ and $R_{18}$ as $C_2$–$C_{20}$-alkylidene are for example ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene.

$R_7$ and $R_{18}$ as $C_7$–$C_{20}$-aralkylidene may be $C_7$–$C_{20}$-phenylalkylidene such as for example benzylidene, 2-phenylethylidene or 1-phenyl-2-hexylidene.

$R_7$ and $R_{18}$ as $C_6$–$C_{10}$-cycloalkylene and $R_{17}$ and $R_{20}$ as $C_6$–$C_{18}$-cycloalkylene may be a saturated hydrocarbon group with two free valencies and at least one cyclic unit.

$R_7$, $R_{17}$, $R_{18}$ and $R_{20}$ are for example cyclohexylene or cyclohexylene substituted by $C_1$–$C_4$-alkyl. Cyclohexylene and methylcyclohexylene are preferred.

In addition $R_{17}$ and $R_{20}$ may be alkylene-cyclohexylene-alkylene with 8 to 18 carbon atoms, cyclohexylene-alkylene-cyclohexylene with 13 to 18 carbon atoms or alkylidenedicyclohexylene with 14 to 18 carbon atoms. Preferred examples are cyclohexylenedimethylene, methylenedicyclohexylene, isopropylidenedicyclohexylene.

$R_7$ as $C_2$–$C_{18}$-alkenylene is for example vinylene, methylvinylene, octenylethylene or dodecenylethylene.

$R_7$ and $R_{18}$ as $C_6$–$C_{10}$-arylene and $R_{17}$ and $R_{20}$ as $C_6$–$C_{18}$-arylene may be substituted or unsubstituted at the aromatic group. $R_7$ and $R_{18}$ are for example 1,2-phenylene, 1,3-phenylene or 1,4-phenylene. $R_{17}$ and $R_{20}$ are preferably phenylene unsubstituted or substituted by $C_1$–$C_4$-alkyl, biphenylene, phenylene-alkylene-phenylene with 13 to 18 carbon atoms, phenylene-alkylidene-phenylene with 14 to 18 carbon atoms, naphthylene. Preferred examples are phenylene, methylphenylene, biphenylene, methylenediphenylene, isopropylidenediphenylene.

$R_8$ as alkalimetal may be Li, Na or K.

If $R_9$ and $R_{10}$ together with the nitrogen atom to which they are bonded form part of a 5-membered to 7-membered heterocyclic group, this group is preferably a saturated heterocyclic group with N and/or O as hetero atoms. Illustrative examples are 1-pyrrolidinyl, 1-piperidyl, 4-morpholinyl, 1hexahydroazepinyl and 4-methyl-1-piperazinyl.

$R_{11}$ as $C_6$–$C_{12}$-aryl is for example phenyl or naphthyl which both may be substituted or unsubstituted. $R_{11}$ is preferably phenyl unsubstituted or substituted by $C_1$–$C_3$-alkyl and/or $C_1$–$C_3$-alkoxy. Examples are phenyl, methylphenyl, dimethylphenyl, trimethylphenyl, methoxyphenyl and ethoxyphenyl.

If the two groups $R_{12}$ together are $C_2$–$C_{12}$-alkylene or $C_6$–$C_{28}$-arylene and together with the phosphorus atom and the two oxygen atoms form a 5-membered to 7-membered heterocyclic ring, the $C_2$–$C_{12}$-alkylene group is preferably a straight chain or branched alkylene group with 2 to 7 carbon atoms and the $C_6$–$C_{28}$-arylene group may be a 1,2-phenylene group unsubstituted or substituted by $C_1$–$C_4$-alkyl or may be a biphenylene group unsubstituted or substituted by $C_1$–$C_4$-alkyl.

Examples for $R_4$ as a group $$-\underset{(O)_r}{\overset{\|}{P}}(OR_{12})_2$$

are:

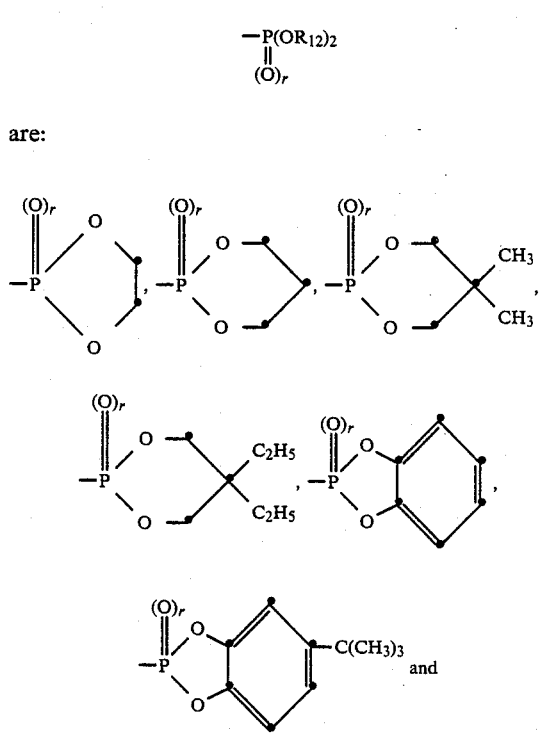

-continued

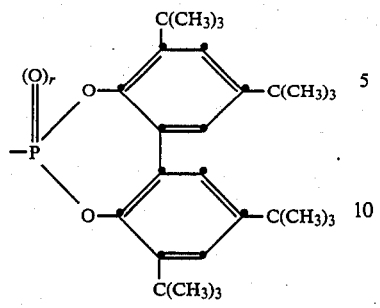

—$XR_{13}$, —$YR_{14}$ and -$ZR_{22}$ as a 5-membered to 7-membered heterocyclic group may be a saturated heterocyclic group with N and/or O as hetero atoms. Illustrative examples are 1-pyrrolidinyl, 1-piperidyl, 4-morpholinyl, 1-hexahydroazepinyl and 4-methyl-1-piperazinyl.

—$ZR_{22}$ may also be halogen, preferably Cl.

$R_{17}$ and $R_{20}$ as $C_2$–$C_{18}$-alkylene are for example ethylene, propylene, trimethylene, tetramethylene, pentamethylene, 2,2-dimethyl-1,3-propanediyl, hexamethylene, octamethylene, decamethylene or dodecamethylene. $C_2$–$C_6$-alkylene is preferred.

$R_{17}$ as $C_4$–$C_{12}$-alkylene which is substituted in the chain by 1 or 2 oxygen atoms is for example 3-oxapentane-1,5-diyl or 3,6-dioxaoctane-1,8-diyl.

$R_{17}$ as $C_4$–$C_8$-alkenylene is for example 2-butene-1,4-diyl.

$R_{17}$ and $R_{20}$ as $C_8$–$C_{12}$-aralkylene are for example alkylene-phenylenealkylene with 8 to 12 carbon atoms, preferably dimethylenephenylene (xylylene) which may optionally be substituted by $C_1$–$C_4$-alkyl.

$R_{18}$ as $C_2$–$C_{12}$-alkylene which is substituted in the chain by 1 or 2 oxygen atoms is for example 2-oxapropane-1,3-diyl, 2,7-dioxaoctane-1,8-diyl or 2,6-dioxa-4,4-dimethyl-1,7-heptanediyl.

$R_{23}$ and $R_{25}$ as $C_1$–$C_4$-alkyl are for example methyl, ethyl, propyl or butyl.

$R_4$ as aliphatic $C_4$–$C_{18}$-triacyl may be $C_4$–$C_{18}$-alkanetrioyl unsubstituted or substituted by OH. Preferred examples are those triacyls derived from methanetricarboxylic, 1,1,2-ethanetricarboxylic, 1,2,3-propanetricarboxylic, citric or 1,2,3-butanetricarboxylic acids.

$R_4$ as aliphatic $C_6$–$C_{18}$-triacyl which is substituted by a nitrogen atom is for example

The group $N(CH_2CO—)_3$ is especially preferred.

$R_4$ as aromatic triacyl having up to 18 carbon atoms is for example a triacyl derived from 1,2,4-benzenetricarboxylic acid or 1,3,5-benzenetricarboxylic acid.

$R_4$ as heterocyclic triacyl having up to 18 carbon atoms is for example

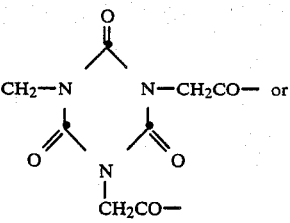

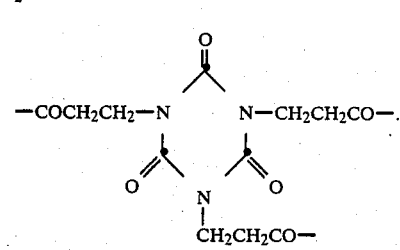

A heterocyclic triacyl group with 9 to 12 carbon atoms is preferred.

$R_4$ as substituted aliphatic tricarbamoyl having up to 24 carbon atoms is for example a group

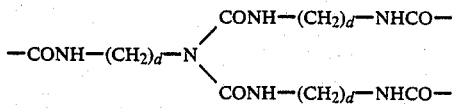

with d being an integer from 2 6, preferably 6.

$R_4$ as aromatic tricarbamoyl having up to 24 carbon atoms is for example benzenetricarbamoyl.

$R_4$ as heterocyclic tricarbamoyl having up to 24 carbon atoms is for example a group

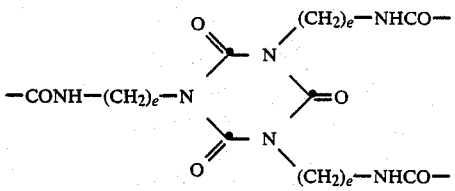

with e being an integer from 2 to 6, preferably 6.

$R_4$ as aliphatic $C_6$–$C_{18}$-tetraacyl may be $C_4$–$C_{18}$-alkanetetraoyl. Preferred examples are those tetraacyls derived from 1,1,3,3-propanetetracarboxylic or 1,2,3,4-butanetetracarboxylic acids.

$R_4$ as aliphatic $C_{10}$–$C_{18}$-tetraacyl which is substituted with two nitrogen atoms is for example a group of the formula

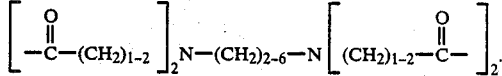

A tetraacyl derived from ethylenediaminetetraacetic acid is preferred.

$R_4$ as aromatic $C_{10}$–$C_{18}$-tetraacyl is for example the tetraacyl derived from 1,2,4,5-benzenetetracarboxylic acid.

$R_4$ as cycloaliphatic $C_{10}$–$C_{22}$-tetraacyl may be a cycloalkanetetracarbonyl with 10 to 22 carbon atoms or a cycloalkenetetracarbonyl with 10 to 22 carbon atoms. Examples are the following groups:

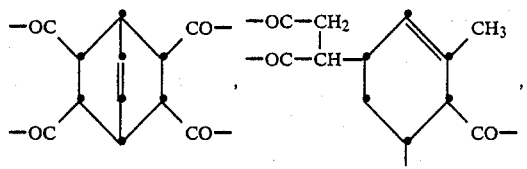

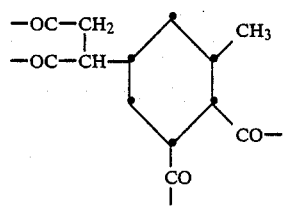

Those compounds of formula (I) are preferred, in which $R_1$ is hydrogen, methyl, allyl, benzyl or acetyl, $R_2$ is hydrogen, $C_1$-$C_{12}$-alkyl, $C_6$-$C_9$-cycloalkyl or $C_6$-$C_9$-aryl, $R_3$ is $C_6$-$C_{12}$-aryl or a group of the formula (II), n is 1, 2 or 3 and, if n is 1, $R_4$ is hydrogen,

—$COR_5$, —$COOR_6$, —CO—$R_7$—$COOR_8$,

—CO—$R_7$—CON—$R_{10}$, —CON—$R_{10}$, —$SO_2R_{11}$ or
　　　　　　　|　　　　　　　|
　　　　　　$R_9$　　　　　　$R_9$

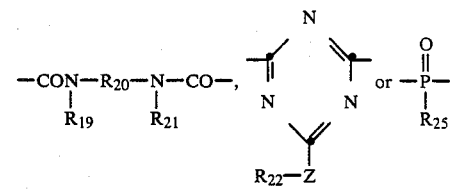

in which $R_5$ is hydrogen, $C_1$-$C_{18}$-alkyl, $C_6$-$C_9$-cycloalkyl, $C_2$-$C_4$-alkenyl, $C_6$-$C_8$-aryl, $C_7$-$C_{16}$-aralkyl or $C_1$-$C_3$-alkyl substituted by a group of the formula (III) where W is —O— or

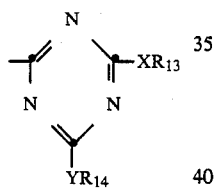

and $R_{15}$ is hydrogen, $C_1$-$C_{12}$-alkyl or $C_6$-$C_9$-cycloalkyl, $R_6$ is $C_1$-$C_{18}$-alkyl, $C_2$-$C_6$-alkyl substituted by $C_1$-$C_4$-alkoxy, $C_6$-$C_{12}$-cycloalkyl or a group of the formula (II), $R_7$ is a direct bond, $C_1$-$C_{10}$-alkylene, $C_6$-$C_8$-cycloalkylene, vinylene or phenylene, $R_8$ is hydrogen, $C_1$-$C_{12}$-alkyl, $C_6$-$C_9$-cycloalkyl, allyl or a group of the formula (II), $R_9$ and $R_{10}$, which are identical or different, are hydrogen, $C_1$-$C_{12}$-alkyl, $C_6$-$C_9$-cycloalkyl, allyl or a group of the formula (II), or, together with the nitrogen atom to which they are bonded, form part of a heterocyclic ring, $R_{11}$ is methyl, ethyl or $C_6$-$C_9$-aryl, $R_{13}$ and $R_{14}$, which are identical or different, are hydrogen, $C_1$-$C_{12}$-alkyl, $C_6$-$C_9$-cycloalkyl, allyl or a group of the formula (II), X and Y, which are identical or different, are —O— or

\\
 N—$R_{16}$,
/ where $R_{16}$ is hydrogen, $C_1$-$C_{12}$-alkyl, OH-monosubstituted $C_2$-$C_4$-alkyl, $C_6$-$C_9$-cycloalkyl, allyl or a group of the formula (II), or the groups $R_{13}X$— and $R_{14}Y$—, which are identical or different, are a 1-pyrrolidinyl, 1-piperidyl, 4-morpholinyl or 1-hexahydroazepinyl group or, if n is 2, $R_4$ is —CO—,

—COO—$R_{17}$—OOC—, —CO—$R_{18}$—CO—,

—CON—$R_{20}$—N—CO—,　　　　　　　or　—P—
　　|　　　　　|　　　　　　　　　　　　　|
　$R_{19}$　　　$R_{21}$　　　　　　　　　　　$R_{25}$ in which $R_{17}$ is $C_2$-$C_{12}$-alkylene, $C_4$-$C_{12}$-alkylene substituted in the chain by 1 or 2 oxygen atoms, $C_6$-$C_{15}$-cycloalkylene, 2-butene-1,4-diyl or a group of the formula (IV) in which $R_{23}$ is hydrogen or methyl, $R_{18}$ is a direct bond, $C_1$-$C_{12}$-alkylene, $C_2$-$C_{12}$-alkylidene, $C_2$-$C_8$-alkylene substituted in the chain by one or two groups

\\
 N—$R_{24}$
/ where $R_{24}$ is $C_1$-$C_8$-alkyl, $C_6$-$C_9$-cycloalkyl or a group of the formula (II), $R_{19}$ and $R_{21}$, which are identical or different, are hydrogen, $C_1$-$C_8$-alkyl, $C_6$-$C_9$-cycloalkyl or a group of the formula (II), $R_{20}$ is $C_2$-$C_{10}$-alkylene, $C_6$-$C_{15}$-cycloalkylene, $C_6$-$C_{15}$-arylene or xylylene, $R_{22}$ is hydrogen, $C_1$-$C_{12}$-alkyl, OH-monosubstituted $C_2$-$C_4$-alkyl, $C_6$-$C_9$-cycloalkyl, allyl or a group of the formula (II) and Z is —O— or

\\
 N—$R_{16}$
/ with $R_{16}$ as defined above, or —$ZR_{22}$ is halogen, $R_{25}$ is $C_1$-$C_4$-alkyl and, if n is 3, $R_4$ is aliphatic $C_4$-$C_8$-triacyl, a group $N(CH_2CO—)_3$, aromatic or heterocyclic triacyl having up to 10 carbon atoms or a 1,3,5-triazine-2,4,6-triyl group.

Those compounds of formula (I) are preferred, in which $R_1$ is hydrogen, methyl, allyl, benzyl or acetyl, $R_2$ is hydrogen, $C_1$-$C_{12}$-alkyl, $C_6$-$C_9$-cycloalkyl or $C_6$-$C_9$-aryl, $R_3$ is $C_6$-$C_{12}$-aryl or a group of the formula (II), n is 1, 2 or 3 and, if n is 1, $R_4$ is hydrogen or one of the groups

—$COR_5$, —$COOR_6$, —CO—$R_7$—$COOR_8$,

—CO—$R_7$—CON—$R_{10}$, —CON—$R_{10}$, —$SO_2R_{11}$,
　　　　　　　|　　　　　　　|
　　　　　　$R_9$　　　　　　$R_9$

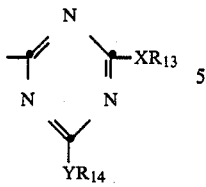

in which $R_5$ is hydrogen, $C_1$-$C_{18}$-alkyl, $C_6$-$C_9$-cycloalkyl, $C_2$-$C_4$-alkenyl, $C_6$-$C_8$-aryl, $C_7$-$C_{16}$-aralkyl or $C_1$-$C_3$-alkyl substituted by a group of the formula (III) where W is —O— or

and $R_{15}$ is hydrogen, $C_1$-$C_{12}$-alkyl or $C_6$-$C_9$-cycloalkyl, $R_6$ is $C_1$-$C_{12}$-alkyl, $C_6$-$C_{12}$-cycloalkyl or a group of the formula (II), $R_7$ is a direct bond, $C_1$-$C_8$-alkylene, $C_6$-$C_8$-cycloalkylene, vinylene or phenylene, $R_8$ is $C_1$-$C_{12}$-alkyl, $C_6$-$C_9$-cycloalkyl, allyl or a group of the formula (II), $R_9$ and $R_{10}$, which can be identical or different, are hydrogen, $C_1$-$C_{12}$-alkyl, $C_6$-$C_9$-cycloalkyl, allyl or a group of the formula (II), or, together with the nitrogen atom to which they are bonded, form part of a heterocyclic ring, such as pyrrolidine, piperidine, morpholine or hexahydroazepine, $R_{11}$ is methyl, ethyl or $C_6$-$C_9$-aryl, $R_{13}$ and $R_{14}$, which can be identical or different, are hydrogen, $C_1$-$C_{12}$-alkyl, $C_6$-$C_9$-cycloalkyl, allyl or a group of the formula (II), X and Y, which can be identical or different, are —O— or

where $R_{16}$ is hydrogen, $C_1$-$C_{12}$-alkyl, $C_6$-$C_9$-cycloalkyl, allyl or a group of the formula (II), or the groups $R_{13}$X— and $R_{14}$Y—, which can be identical or different, are a 1-pyrrolidinyl, 1-piperidyl, 4-morpholinyl or 1-hexahydroazepinyl group or, if n is 2, $R_4$ is a —CO— group or one of the groups

—COO—$R_{17}$—OOC—,  —CO—$R_{18}$—CO—,

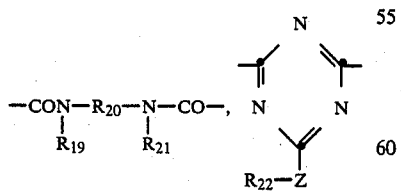

in which $R_{17}$ is $C_2$-$C_{10}$-alkylene, $C_6$-$C_{15}$-cycloalkylene, 2-butene-1,4-diyl or a group of the formula (IV) in which $R_{23}$ is hydrogen or methyl, $R_{18}$ is a direct bond, $C_1$-$C_{12}$-alkylene, $C_2$-$C_{12}$-alkylidene, $C_2$-$C_8$-alkylene substituted in the chain by one or two groups

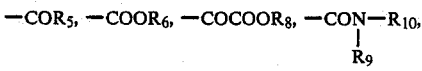

where $R_{24}$ is $C_1$-$C_8$-alkyl, $C_6$-$C_9$-cycloalkyl or a group of the formula (II), $R_{19}$ and $R_{21}$, which can be identical or different, are hydrogen, $C_1$-$C_8$-alkyl, $C_6$-$C_9$-cycloalkyl or a group of the formula (II), $R_{20}$ is $C_2$-$C_{10}$-alkylene, $C_6$-$C_{15}$-cycloalkylene, $C_6$-$C_{15}$-arylene or xylylene, $R_{22}$ is hydrogen, $C_1$-$C_{12}$-alkyl, $C_6$-$C_9$-cycloalkyl, allyl or a group of the formula (II) and Z is —O— or

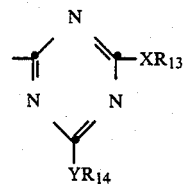

with $R_{16}$ as defined above, or, if n is 3, $R_4$ is aliphatic $C_4$-$C_8$-triacyl, a group N(CH$_2$CO—)$_3$, aromatic or heterocyclic triacyl having up to 10 carbon atoms or a 1,3,5-triazine-2,4,6-triyl group.

Those compounds of formula (I) are particularly preferred, in which $R_1$ is hydrogen or methyl, $R_2$ is hydrogen or methyl, $R_3$ is 2,2,6,6-tetramethyl-4-piperidyl or 1,2,2,6,6-pentamethyl-4-piperidyl, n is 1, 2 or 3 and, if n is 1, $R_4$ is hydrogen or one of the groups —COR$_5$, —COOR$_6$, —COCOOR$_8$, —CON—R$_{10}$,
                                          |
                                          R$_9$

in which $R_5$ is $C_1$-$C_{17}$-alkyl, cyclohexyl or phenyl, $R_6$ is $C_2$-$C_{18}$-alkyl, $C_6$-$C_{10}$-cycloalkyl or a group of the formula (II) with $R_1$ being hydrogen or methyl, $R_8$ is $C_2$-$C_{12}$-alkyl, cyclohexyl or a group of the formula (II) with $R_1$ being hydrogen or methyl, $R_9$ is hydrogen, $R_{10}$ is $C_4$-$C_{12}$-alkyl or cyclohexyl, $R_{13}$ and $R_{14}$, which can be identical or different, are $C_1$-$C_{12}$-alkyl, cyclohexyl, allyl or a group of the formula (II) with $R_1$ being hydrogen or methyl, and X and Y, which can be identical or different, are a group

>N—R$_{16}$ where $R_{16}$ is hydrogen, $C_1$-$C_{12}$-alkyl, cyclohexyl, allyl or a group of the formula (II) with $R_1$ being hydrogen or methyl and, if n is 2, $R_4$ is one of the groups

—COO—$R_{17}$—OOC—,  —CO—$R_{18}$—CO—,

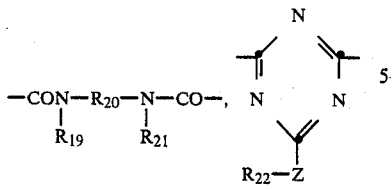
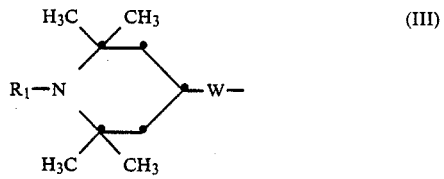

in which $R_{17}$ is $C_4-C_{10}$-alkylene, $C_6-C_8$-cycloalkylene or a group of the formula (IV) in which $R_{23}$ is hydrogen, $R_{18}$ is a direct bond, $C_1-C_8$-alkylene, $C_2-C_8$-alkylidene, cyclohexylene or phenylene, $R_{19}$ and $R_{21}$ are hydrogen, $R_{20}$ is $C_6-C_9$-alkylene or $C_6-C_{13}$-arylene, $R_{22}$ is $C_1-C_{12}$-alkyl, cyclohexyl, allyl or a group of the formula (II) with $R_1$ being hydrogen or methyl, and Z is —O— or

with $R_{16}$ being as defined above, and, if n is 3, $R_4$ is a 1,3,5-triazine-2,4,6-triyl group.

$R_1$ is preferably hydrogen, $C_1-C_4$-alkyl, allyl, benzyl or acetyl, in particular hydrogen or methyl.

Compounds of formula (I) wherein $R_2$ is hydrogen, $C_1-C_4$-alkyl, cyclohexyl, phenyl or benzyl and $R_3$ is phenyl unsubstituted or substituted by $C_2-C_4$-alkoxycarbonyl or is a group of the formula (II) are preferred.

Compounds of formula (I) wherein $R_1$ is hydrogen or methyl, $R_2$ is hydrogen or $C_1-C_4$-alkyl and $R_3$ is phenyl substituted by $C_2-C_4$-alkoxycarbonyl or is a group of formula (II) are particularly preferred.

Those compounds of formula (I) are of interest, wherein n is 1, 2 or 3 and, if n=1, $R_4$ is hydrogen, CN,

—$COR_5$, —$COOR_6$, —$CO-R_7-COOR_8$,

—$CO-R_7-CON-R_{10}$, —$CON-R_{10}$, —$SO_2R_{11}$ or
     |                |
     $R_9$            $R_9$

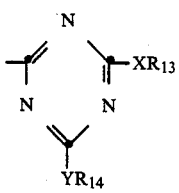

in which $R_5$ is hydrogen, $C_1-C_{18}$-alkyl, cyclopentyl, cyclohexyl unsubstituted or substituted by $C_1-C_4$-alkyl, $C_2-C_{18}$-alkenyl, phenyl unsubstituted or substituted by $C_1-C_4$-alkyl, by $C_1-C_4$-alkoxy and/or by OH, $C_7-C_{10}$-phenylalkyl unsubstituted or substituted at the phenyl ring by $C_1-C_4$-alkyl and/or by OH, $C_1-C_{10}$-alkyl substituted by $C_1-C_{18}$-alkoxy, by $C_2-C_{18}$-dialkylamino or by a group of the formula (III)

where $R_1$ is hydrogen, O·, CN, NO, cyanomethyl, $C_1-C_{12}$-alkyl, $C_3-C_{12}$-alkenyl or $C_3-C_{12}$-alkynyl subject to the proviso that the carbon atom attached to the nitrogen atom is a primary carbon atom, $C_7-C_{12}$-aralkyl, $C_1-C_{12}$-acyl, 2,3-epoxypropyl, OH-monosubstituted $C_2-C_6$-alkyl or 2,3-dihydroxypropyl and W is —O— or

where $R_{15}$ is hydrogen, $C_1-C_{18}$-alkyl, cyclopentyl, cyclohexyl unsubstituted or substituted by $C_1-C_4$-alkyl, $C_3-C_{18}$-alkenyl, phenyl unsubstituted or substituted by $C_1-C_4$-alkyl, by $C_1-C_4$-alkoxy and/or by OH, $C_7-C_{10}$-phenylalkyl unsubstituted or substituted at the phenyl ring by $C_1-C_4$-alkyl and/or by OH, or is a group of the formula (II), $R_6$ is $C_1-C_{18}$-alkyl, $C_2-C_6$-alkyl substituted by OH, by $C_1-C_{18}$-alkoxy or by $C_2-C_{18}$-dialkylamino, cyclopentyl, cyclohexyl unsubstituted or substituted by $C_1-C_4$-alkyl, or is $C_3-C_{18}$-alkenyl, phenyl unsubstituted or substituted by $C_1-C_4$-alkyl and/or by $C_1-C_4$-alkoxy, $C_7-C_{10}$-phenylalkyl unsubstituted or substituted at the phenyl ring by $C_1-C_4$-alkyl and/or by OH, or is a group of the formula (II), $R_7$ is a direct bond, $C_1-C_{18}$-alkylene, $C_2-C_{20}$-alkylidene, $C_7-C_{20}$-phenylalkylidene, cyclohexylene unsubstituted or substituted by $C_1-C_4$-alkyl, $C_2-C_{18}$-alkenylene or phenylene, $R_8$ is as defined for $R_6$ or is hydrogen or an alkali metal, $R_9$ and $R_{10}$, which are identical or different, are as defined for $R_{15}$, or $R_9$ and $R_{10}$, together with the nitrogen atom to which they are bonded, form a pyrrolidine, piperidine, morpholine or hexahydroazepine group, $R_{11}$ is $C_1-C_{12}$-alkyl or phenyl unsubstituted or substituted by $C_1-C_3$-alkyl and/or by $C_1-C_3$-alkoxy, $R_{13}$ and $R_{14}$, which are identical or different, are as defined for $R_6$ or are hydrogen, and X and Y, which are identical or different, are a different bond, —O— or

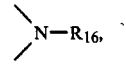

where $R_{16}$ is as defined for $R_{15}$ or is OH-monosubstituted $C_2-C_6$-alkyl, or the groups $R_{13}X$— and $R_{14}Y$—, which are identical or different, are a 1-pyrrolidinyl, 1-piperidyl, 4-morpholinyl, 1-hexahydroazepinyl or 4-methyl-1-piperazinyl group, or, if n=2, $R_4$ is

—CO—, —$SO_2$—, —COO—$R_{17}$—OOC—, —CO—$R_{18}$—CO—,

-continued

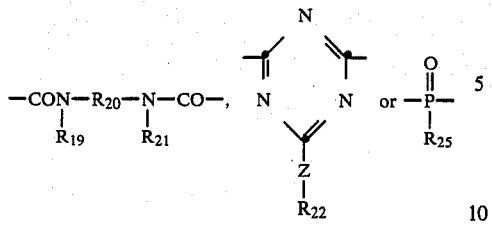

in which $R_{17}$ is $C_2$–$C_{18}$-alkylene, $C_4$–$C_{12}$-alkylene substituted in the chain by 1 or 2 oxygen atoms, cyclohexylene, $C_8$–$C_{18}$-cyclohexylenedialkylene, $C_{13}$–$C_{18}$-alkylenedicyclohexylene, $C_{14}$–$C_{18}$-alkylidenedicyclohexylene, $C_4$–$C_8$-alkenylene, phenylene, xylylene or a group of the formula (IV)

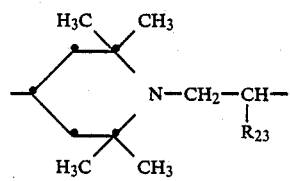

where $R_{23}$ is hydrogen, $C_1$–$C_4$-alkyl or phenyl, $R_{18}$ is a direct bond, $C_1$–$C_{18}$-alkylene, $C_2$–$C_{20}$-alkylidene, $C_7$–$C_{20}$-phenylalkylidene, cyclohexylene unsubstituted or substituted by $C_1$–$C_4$-alkyl, phenylene, $C_2$–$C_{12}$-alkylene substituted in the chain by 1 or 2 oxygen atoms or by 1 or 2 groups

where $R_{24}$ is as defined for $R_{15}$, $R_{19}$ and $R_{21}$, which are identical or different, are as defined for $R_{15}$, $R_{20}$ in $C_2$–$C_{18}$-alkylene, cyclohexylene unsubstituted or substituted by $C_1$–$C_4$-alkyl, $C_8$–$C_{18}$-cyclohexylenedialkylene, $C_{13}$–$C_{18}$-alkylenedicyclohexylene, phenylene, xylylene, $R_{22}$ is as defined for $R_{13}$ and $R_{14}$, Z is as defined for X and Y, or $-ZR_{22}$ is 1-pyrrolidinyl, 1-piperidyl, 4-morpholinyl, 1-hexahydroazepinyl or 4-methyl-1-piperazinyl or halogen, $R_{25}$ is $C_1$–$C_4$-alkyl, or, if n=3, $R_4$ is $C_4$–$C_{18}$-alkanetrioyl unsubstituted or substituted by OH, $N(CH_2CO-)_3$, benzenetricarbonyl or a group

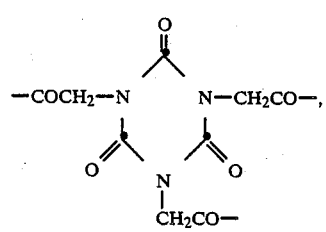

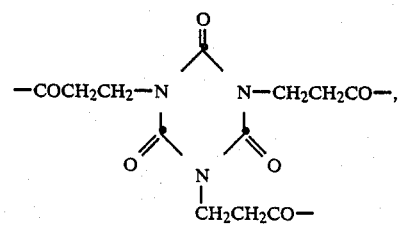

-continued

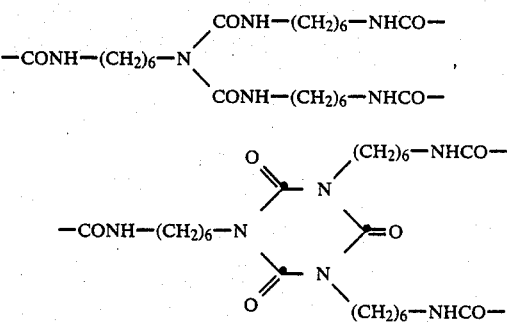

or is benzenetricarbamoyl or a 1,3,5-triazine-2,4,6-triyl group, a $\equiv$P group, a $\equiv$PO group or a group $(-CO-R_7-COO)_3Al$ with $R_7$ as defined above.

n is preferably 1, 2 or 3, in particular 1 or 2.

Compounds of formula (I) wherein $R_3$ is a group of the formula (II) are preferred.

If n is 1, $R_4$ is in particular $-COR_5$, $-COOR_6$ or

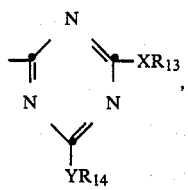

and if n is 2, $R_4$ is preferably $-COO-R_{17}-OOC-$, $-CO-R_{18}-CO-$ or 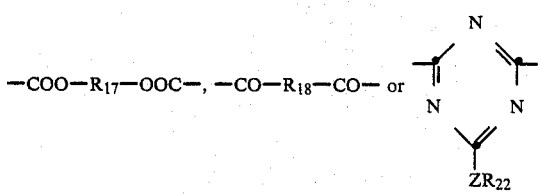

Those compounds of formula (I) are preferred, wherein n is 1, 2 or 3 and, if n=1, $R_4$ is selected from the group consisting of hydrogen, $-COR_5$, $-COOR_6$, $-CO-R_7-COOR_8$, $-CON-R_{10}$ and 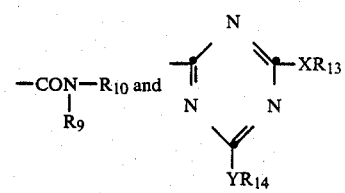
    |
    $R_9$ wherein $R_5$ is $C_1$–$C_{18}$-alkyl, $R_6$ is $C_1$–$C_{18}$-alkyl, $C_2$–$C_6$-alkyl substituted by $C_1$–$C_4$-alkoxy, cyclohexyl unsubstituted or substituted by $C_1$–$C_4$-alkyl or is a group of the formula (II), $R_7$ is $C_1$–$C_{10}$-alkylene, $R_8$ is hydrogen, $R_9$ and $R_{10}$ are independently hydrogen, $C_1$–$C_4$-alkyl or cyclohexyl, $R_{13}$ and $R_{14}$ are independently hydrogen, $C_1$–$C_8$-alkyl, allyl or a group of formula (II), X and Y are independently $-O-$ or

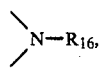

$R_{16}$ is hydrogen, $C_1$–$C_8$-alkyl, OH-monosubstituted $C_2$–$C_4$-alkyl, allyl or a group of the formula (II), if n=2, $R_4$ is selected from the group consisting of —COO—$R_{17}$—OOC—,

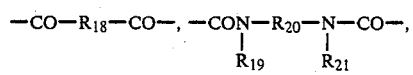

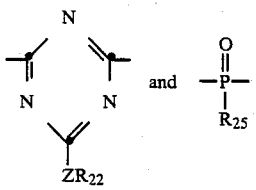

wherein $R_{17}$ is $C_2$–$C_{12}$-alkylene or $C_4$–$C_{12}$-alkylene substituted in the chain by 1 or 2 oxygen atoms, $R_{18}$ is a direct bond or $C_1$–$C_{10}$-alkylene, $R_{19}$ and $R_{21}$ are hydrogen, $R_{20}$ is $C_2$–$C_{10}$-alkylene or cyclohexylene unsubstituted or substituted by $C_1$–$C_4$-alkyl, $R_{22}$ is $C_1$–$C_8$-alkyl, OH-monosubstituted $C_2$–$C_4$-alkyl or allyl, Z is —O— or

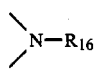

with $R_{16}$ being as defined above or —$ZR_{22}$ is halogen, $R_{25}$ is $C_1$–$C_4$-alkyl and, if n=3, $R_4$ is 1,3,5-triazine-2,4,6-triyl.

Those compounds of formula (I) are particularly preferred, wherein $R_1$ is hydrogen, $R_2$ is hydrogen or methyl, $R_3$ is 2,2,6,6-tetramethyl-4-piperidyl, n is 1, 2 or 3 and, if n is 1, $R_4$ is —COR$_5$, —COOR$_6$ or

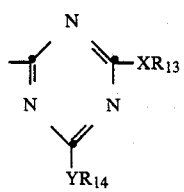

in which $R_5$ is $C_1$–$C_{18}$-alkyl, $R_6$ is $C_1$–$C_{18}$-alkyl, cyclohexyl, 4-t-butylcyclohexyl or 1,2,2,6,6-pentamethyl-4-piperidyl, $R_{13}$ and $R_{14}$ are independently $C_1$–$C_8$-alkyl or allyl, X and Y are independently —O— or

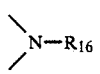

with $R_{16}$ being hydrogen, $C_1$–$C_8$-alkyl, allyl or 2,2,6,6-tetramethyl-4-piperidyl and, if n is 2, $R_4$ is —COO—$R_{17}$—OOC—, —CO—$R_{18}$—CO— or 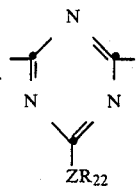

in which $R_{17}$ is $C_4$–$C_6$-alkylene, $R_{18}$ is a direct bond or $C_1$–$C_8$-alkylene, $R_{22}$ is $C_1$–$C_8$-alkyl or allyl and Z is —O— or

with $R_{16}$ being as defined above and, if n is 3, $R_4$ is a 1,3,5-triazine-2,4,6-triyl group.

Those compounds of formula (I) are of interest, wherein $R_1$ is hydrogen, $R_2$ is hydrogen or methyl, $R_3$ is 2,2,6,6-tetramethyl-4-piperidyl, n is 1 or 2 and, if n is 1, $R_4$ is —COOR$_6$ or

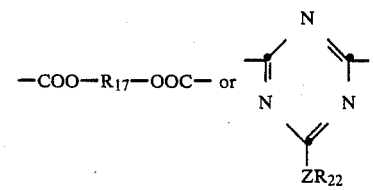

in which $R_6$ is $C_4$–$C_{18}$-alkyl, cyclohexyl, 4-t-butylcyclohexyl or 1,2,2,6,6-pentamethyl-4-piperidyl, $R_{13}$ and $R_{14}$ are independently $C_1$–$C_4$-alkyl, X and Y are with $R_{16}$ being 2,2,6,6-tetramethyl-4-piperidyl and, if n is 2, $R_4$ is —COO—$R_{17}$—OOC— or in which $R_{17}$ is $C_4$–$C_6$-alkylene, $R_{22}$ is $C_1$–$C_4$-alkyl and Z is —O— or with $R_{16}$ being hydrogen, $C_1$–$C_4$-alkyl or allyl.

Especially preferred examples of compounds of formula (I) are:

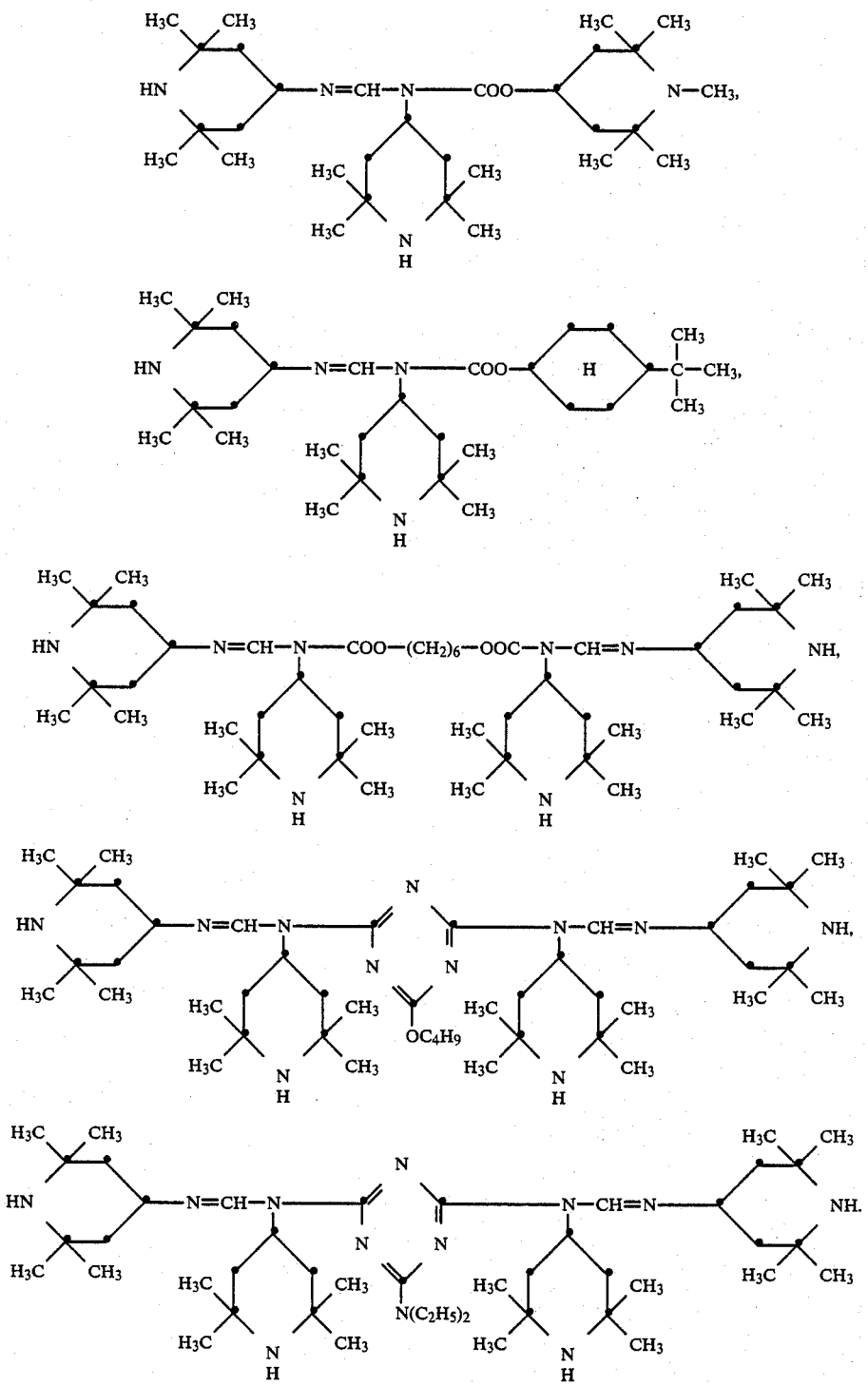

The compounds of the formula (I) may be obtained by two different procedures, depending on the nature of the group $R_3$, for example first preparing the compounds with $n=1$ and $R_4=H$; from these, the compounds with $n=1, 2, 3$ or $4$ and $R_4 \neq H$ may be prepared by reaction with suitable acylating agents.

If $R_3$ is a group of the formula (II), the corresponding compounds of the formula (I) can be prepared for example in accordance with scheme 1, by reacting 2 moles of a piperidylamine (V) with 1 mol of an orthoester (VI) in which R' is $C_1$-$C_4$-alkyl, the amidine (VII) being formed with elimination of the alcohol R'OH. The compounds of the formula (I) with $R_3$ being a group of the formula (II) and $R_4 \neq H$ may be then obtained from the compounds of the formual (VII) by acylation.

SCHEME 1

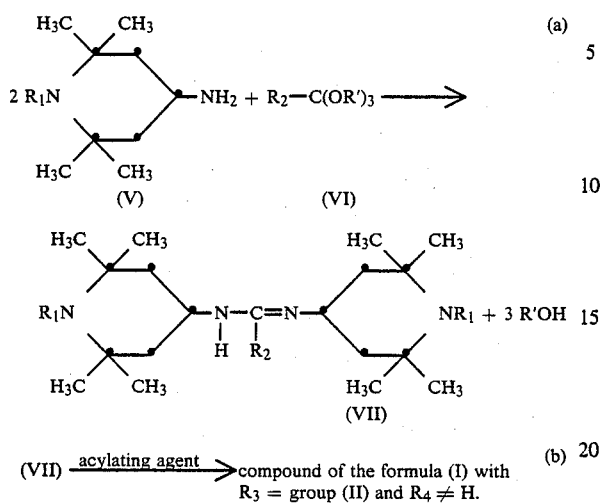

If R$_3$ is C$_6$-C$_{18}$-aryl, the corresponding compounds of the formula (I) can be prepared for example in accordance with scheme 2, by reacting a piperidylamine (V) with an alkylimidate (VIII) in which R' is as defined above, the amidine (IX) being formed with elimination of the alcohol R'OH.

The compounds of the formula (I) with R$_3$=C$_6$-C$_{18}$-aryl and R$_4 \neq$H may be then prepared from the compounds of the formula (IX) by acylation.

SCHEME 2

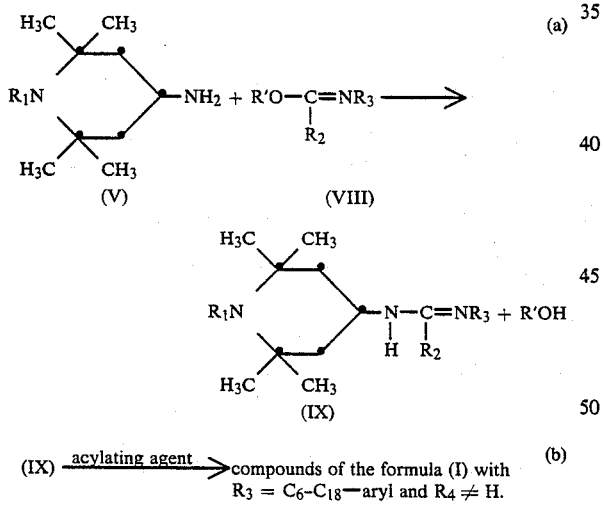

The reaction (a) in schemes 1 and 2 can be carried out for example with or without an inert solvent, operating at a temperature from 80° to 250° C., preferably from 100° to 180° C., with removal of the alcohol liberated in the reaction.

The ratio of the reagents is not critical, and it is possible to use an excess of one or the other of the reagents.

The subsequent acylation reactions (b) in schemes (1) and (2) can be carried out preferably in an inert solvent at a temperature from −20° to 200° C., preferably from 0° to 180° C.; the reaction conditions depend on the type of acylating agent used.

If an acyl halide is used as the acylating agent, the hydrohalic acid liberated in the reaction is neutralized preferably with an inorganic base, such as e.g. sodium or potassium hydroxide or carbonate, in a quantity at least equivalent to the acid liberated in the reaction. The reactions according to schemes (1) and (2) can be carried out in a single reactor without isolation of the amidine (VII) or (IX), but it is also possible to separate these compounds off and to employ them after purification in the subsequent acylation reactions.

In order to illustrate the present invention more clearly, several examples of the preparation of compounds of the formula (I) are described below; these examples are given by way of illustration only and do not imply any restriction.

EXAMPLE 1

93.76 g (0.6 mol) of 2,2,6,6-tetramethyl-4-piperidylamine and 88.92 g (0.6 mol) of triethyl orthoformate are heated to 140°-150° C., with removal of the ethanol liberated in the reaction.

Heating is continued until the evolution of ethanol ceases. After cooling the precipitate formed is separated off by filtration, washed with n-hexane and dried. This gives the compound of the formula

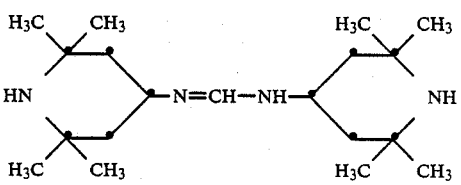

of melting point 175°-176° C.

Analysis for C$_{19}$H$_{38}$N$_4$: Calculated: C 70.75%; H 11.87%; N 17.37%; Found: C 70.78%; H 11.96%; N 17.32%.

EXAMPLES 2 AND 3

Following the procedure of Example 1, and using the appropriate reagents, the following compounds of the general formula

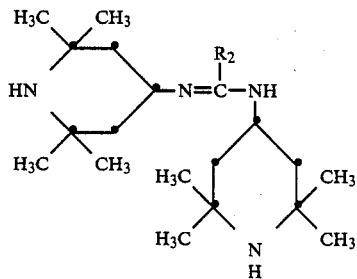

are prepared:

| Example | R$_2$ | Melting point (°C.) |
|---|---|---|
| 2 | CH$_3$— | 93–94 |
| 3 | C$_2$H$_5$— | 45–46 |

EXAMPLE 4

To a suspension of 32.25 g (0.1 mol) of N,N'-bis-(2,2,6,6-tetramethyl-4-piperidyl)-formamidine (prepared as described in Example 1) in 150 ml of dichloromethane, cooled to 0° to +5° C., a solution of 11.39 g (0.105 mol) of ethyl chloroformate in 30 ml of dichloromethane is added slowly, while not exceeding 10° C. After the end of the addition, the mixture is stirred for 2 hours, allowing the temperature to rise up to 20° C., and is then again cooled to about 5° C., and a solution of 4.4 g (0.11 mol) of sodium hydroxide in 30 ml of water is slowly added, while not exceeding 10° C. After the end of the addition, stirring is continued for 2 hours, allowing the temperature to rise up to 20° C.

The organic phase is separated off, washed with water, dried over $Na_2SO_4$ and evaporated to dryness.

The residue obtained is crystallized from ethyl acetate.

This gives the compound of the formula

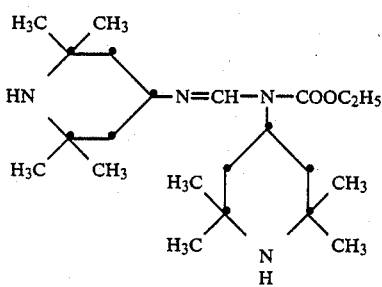

of melting point 123°–124° C.

Analysis for $C_{22}H_{42}N_4O_2$: Calculated: C 66.96%; H 10.73%; N 14.20%; Found: C 66.65%; H 10.71%; N 14.06%.

EXAMPLES 5–28

Following the procedure of Example 4, and using the appropriate reagents, the following compounds of the general formula

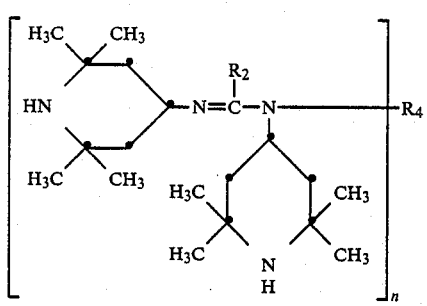

are prepared:

| Example | n | $R_2$ | $R_4$ | Melting point °C. |
|---|---|---|---|---|
| 5 | 1 | H— | —COOC$_4$H$_9$ | 89–90 |
| 6 | 1 | H— | 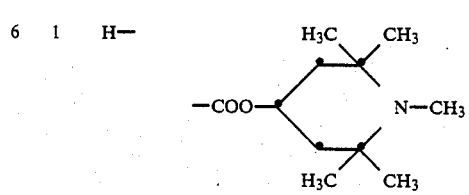 | 172–173 |
| 7 | 1 | H— | —COC$_7$H$_{15}$ | oil |
| 8 | 2 | H— | —COO—(CH$_2$)$_4$—OOC— | 172–173 |
| 9 | 2 | H— | —CO—(CH$_2$)$_8$—CO— | 148–149 |
| 10 | 1 | CH$_3$— | —COOC$_2$H$_5$ | oil |
| 11 | 1 | C$_2$H$_5$— | —COOC$_2$H$_5$ | oil |
| 12 | 1 | CH$_3$— | —COOC$_4$H$_9$ | 92–94 |
| 13 | 1 | H | —COO—⟨piperidinyl with C(CH$_3$)$_3$⟩ | 157–158 |
| 14 | 2 | H | —COO—(CH$_2$)$_6$—OOC— | 165–167 |
| 15 | 2 | H | —COCO— | 262–263 |
| 16 | 2 | H | —CO—(CH$_2$)$_4$—CO— | 155–156 |
| 17 | 1 | H | —COC$_17$H$_{35}$ | wax |
| 18 | 2 | H | —CO(CH$_2$)$_2$CO— | 238–240 |
| 19 | 1 | H | —CO—C(CH$_3$)$_3$ | 125–126 |
| 20 | 1 | H | —COCH$_3$ | 127–129 |
| 21 | 1 | H | —COOCH$_2$CH(C$_2$H$_5$)—(CH$_2$)$_3$—CH$_3$ | 55–56 |
| 22 | 1 | H | —COOCH$_2$CH$_2$OCH$_3$ | 94–95 |
| 23 | 2 | H | —COO(CH$_2$)$_2$O(CH$_2$)$_2$OOC— | 140–141 |
| 24 | 2 | H | —P(=O)(CH$_3$)— | 162–163 |
| 25 | 1 | H | —COOC$_{18}$H$_{37}$ | 69–70 |
| 26 | 1 | H | —COOC$_{14}$H$_{29}$ | 55–56 |
| 27 | 1 | H | —COC$_{11}$H$_{23}$ | 60–62 |
| 28 | 1 | H | —CO(CH$_2$)$_2$COOH | 185–186 |

EXAMPLE 29

64.5 g (0.2 mol) of N,N'-bis-(2,2,6,6-tetramethyl-4-piperidyl)-formamidine are added slowly to a solution of 18.45 g (0.1 mole) of cyanuric chloride in 500 ml of xylene cooled to 10° C., maintaining the temperature between 10° and 15° C.

After the end of the addition, the mixture is heated for 2 hours at 50°–55° C., 53 g (0.5 mol) of anhydrous ground $Na_2CO_3$ are added, and the mixture is heated for 3 hours at 70° C. and then filtered hot.

A white solid precipitates from the filtered solution, and this is separated off by filtration and dried.

This gives the compound of the formula

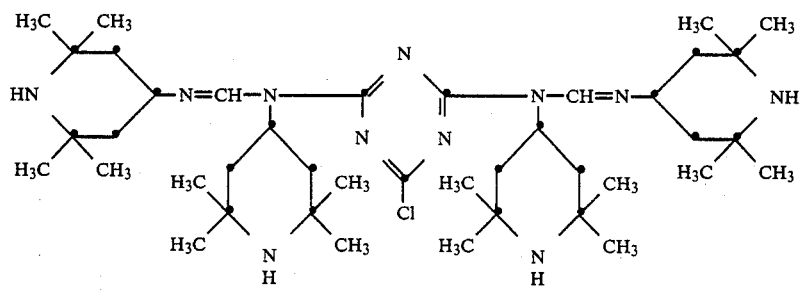

of melting point 206°–207° C.

Analysis for $C_{41}H_{74}ClN_{11}$: Calculated: Cl=4.69%; Found: Cl=4.71%.

EXAMPLE 30

158 g (0.49 mol) of N,N'-bis-(2,2,6,6-tetramethyl-4-piperidyl)-formamidine are added slowly to a solution of 27.7 g (0.15 mol) of cyanuric chloride in 300 ml of trimethylbenzene, maintaining the temperature at 25°–30° C.

The mixture is then heated for one hour to 100°–110° C., 18.9 g of powdered sodium hydroxide are added, and heating is continued under reflux for 12 hours with azeotropic removal of the water of reaction.

The mixture is diluted with 100 ml of trimethylbenzene, cooled and filtered.

The residue obtained after dryness is washed with water and then with methyl ethyl ketone, and then dried again.

This gives the compound of the formula

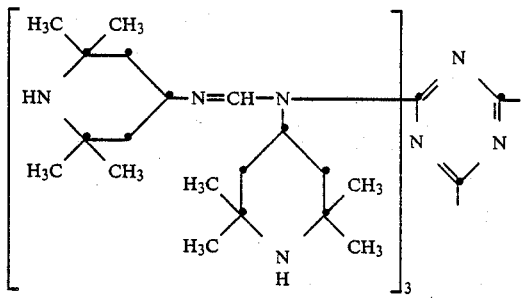

of melting point 295°–296° C.

Analysis for $C_{60}H_{111}N_{15}$: Calculated: C 69.12%; H 10.73%; N 20.15%; Found: C 68.77%; H 10.72%; N 20.01%.

EXAMPLES 34–43

Following the procedure of Example 30, and using the appropriate reagents, the following compounds of the general formula

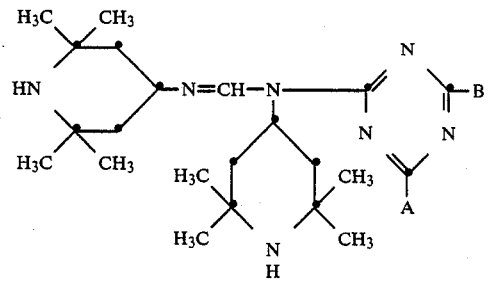

are prepared:

| Example | A | B | Melting point °C. |
|---|---|---|---|
| 31 | H3C\_CH3 / HN—⟨⟩—N—C4H9 / H3C\_CH3 | H3C\_CH3 / HN—⟨⟩—N—C4H9 / H3C\_CH3 | 224–225 |
| 32 | H3C\_CH3 / HN—⟨⟩—N—C2H5 / H3C\_CH3 | H3C\_CH3 / HN—⟨⟩—N—C2H5 / H3C\_CH3 | 176–177 |

-continued

| Example | A | B | Melting point °C. |
|---|---|---|---|
| 33 | 2,2,6,6-tetramethyl-4-(HN)-piperidinyl —N=CH—N— linked to 2,2,6,6-tetramethylpiperidin-4-yl (NH) | C₄H₉O— | 236–237 |
| 34 | 2,2,6,6-tetramethyl-4-(HN)-piperidinyl —N=CH—N— linked to 2,2,6,6-tetramethylpiperidin-4-yl (NH) | (C₂H₅)₂—N— | 232–234 |
| 35 | 2,2,6,6-tetramethyl-4-(HN)-piperidinyl —N=CH—N— linked to 2,2,6,6-tetramethylpiperidin-4-yl (NH) | —NHCH₂CH=CH₂ | 246–248 |
| 36 | —N(CH₂CH=CH₂)₂ | —N(CH₂CH=CH₂)₂ | 198–200 |
| 37 | —NHCH₂CH=CH₂ | —NHCH₂CH=CH₂ | 159–160 |
| 38 | 2,2,6,6-tetramethyl-4-(HN)-piperidinyl —N=CH—N— linked to 2,2,6,6-tetramethylpiperidin-4-yl (NH) | —OC₃H₇iso | 226–227 |
| 39 | 2,2,6,6-tetramethyl-4-(HN)-piperidinyl —N=CH—N— linked to 2,2,6,6-tetramethylpiperidin-4-yl (NH) | —N(CH₃)₂ | 205–206 |

-continued

| Example | A | B | Melting point °C. |
|---|---|---|---|
| 40 | [structure with HN, piperidyl-N=CH-N-piperidyl] | —N(C₄H₉)₂ | 199–200 |
| 41 | [structure with HN, piperidyl-N=CH-N-piperidyl] | —N(CH₂CH=CH₂)₂ | 215–216 |
| 42 | [structure with HN, piperidyl-N=CH-N-piperidyl] | —N(CH₂CH₂OH)₂ | 210–212 |
| 43 | —N(C₂H₅)₂ | —N(C₂H₅)₂ | 121–122 |

EXAMPLE 44

165.2 g (1 mol) of ethyl 4-aminobenzoate and 296.4 g (2 mol) of triethyl orthoformate are heated for 2 hours at 110° C., separating off the ethanol liberated in the reaction. The excess triethyl orthoformate is removed by heating to 110° C. in vacuo (24 mbar). The mixture is cooled, diluted with 600 ml of n-hexane, heated under reflux for 30 minutes and then allowed to cool, and the solid which has separated out is filtered off, washed with 300 ml of hexane and dried.

55.3 g (0.25 mol) of ethyl (4-ethoxycarbonylphenyl)-formimidate thus obtained and 39 g (0.25 mol) of 2,2,6,6-tetramethyl-4-piperidylamine are heated for 6 hours at 100° C. After cooling, 200 ml of acetone are added and the mixture is filtered.

The product obtained is washed with acetone and dried.

This gives a compound of the formula

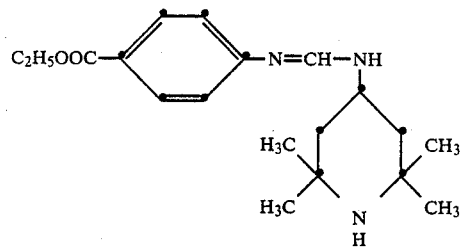

of melting point 110°–111° C.

Analysis for C₁₉H₂₉N₃O₂: Calculated: C 68.85%; H 8.82%; N 12.68%; Found: C 68.89%; H 8.90%; N 12.80%.

EXAMPLE 45

A solution of 8.58 g (0.051 mol) of hexamethylene diisocyanate in 20 ml of toluene is added slowly to 33.15 g (0.1 mol) of N-(2,2,6,6-tetramethyl-4-piperidyl)-N'-(4-ethoxycarbonylphenyl)formamidine (prepared as described in Example 44), dissolved in 100 ml of toluene. The mixture is then heated for 4 hours at 80° C. and evaporated to dryness under reduced pressure (26.7 mbar). The solid obtained is crystallized from acetone.

This gives the compound of the formula

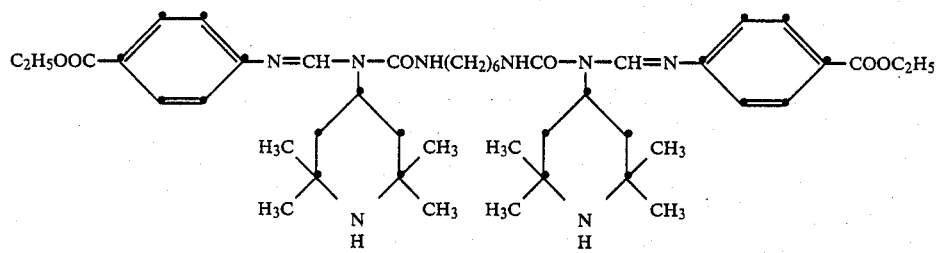

of melting point 151°–152° C.

Analysis for $C_{46}H_{70}N_8O_6$: Calculated: C 69.15%; H 7.81%; N 12.40%; Found: C 69.01%; H 7.86%; N 12.28%.

EXAMPLES 46–48

Following the procedure of Example 45, and using the appropriate reagents, the following compounds are prepared:

After addition, the mixture is stirred, heating under reflux for 8 hours.

Then the mixture is cooled to about 5° C. and a solution of 4.4 g (0.11 mol) of sodium hydroxide in 30 ml of water is slowly added, while not exceeding 10° C.

After addition, stirring is continued for 1 hour, allowing the temperature to rise up to 20° C.

The organic phase is separated off, washed with water and dried over $Na_2SO_4$. The solvent is evapo-

| Ex. | Formula | Melting point °C. |
|---|---|---|
| 46 | | 172–173 |
| 47 | | 199–200 |
| 48 | | 168–169 |

EXAMPLE 49

To a suspension of 32.25 g (0.1 mol) of N,N'-bis(2,2,6,6-tetramethyl-4-piperidyl)-formamidine (prepared as described in Example 1) in 150 ml of dichloromethane, cooled to 0° to 5° C., a solution of 14.24 g (0.105 mol) of diethyl carbamoylchloride in 30 ml of dichloromethane is added slowly while not exceeding 10° C.

rated and the residue obtained is crystallized from n-hexane.

This gives the compound of the formula

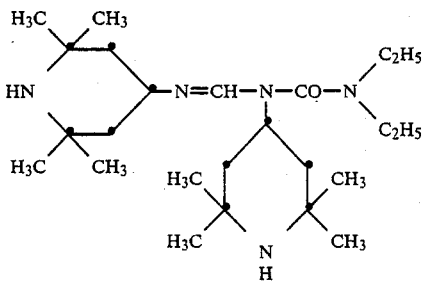

of melting point 90°–91° C.

Analysis for $C_{24}H_{47}N_5O$: Calculated: C 68.36%; H 11.23%; N 16.61%; Found: C 68.01%; H 11.20%; N 16.33%.

EXAMPLE 50

To a suspension of 80.60 g (0.25 mol) of N,N'-bis(2,2,6,6-tetramethyl-4-piperidyl)-formamidine (prepared as described in Example 1) in 600 ml of dichloromethane, cooled to 0° to 5° C., a solution of 43.10 g (0.25 mol) of diethylchlorophosphate in 100 ml of dichloromethane is added slowly, while not exceeding 10° C. After addition the mixture is stirred for 2 hours allowing the temperature to rise up to 20° C., and then it is cooled again to about 5° C.

A solution of 10.8 g (0.27 mol) of sodium hydroxide in 100 ml of water is slowly added, while not exceeding 10° C.

After addition, stirring is continued for 2 hours, allowing the temperature to rise up to 20° C.

The organic phase is separated off, washed with water, dried over $Na_2SO_4$ and evaporated to dryness.

The residue obtained is crystallized from octane.

This gives the compound of the formula

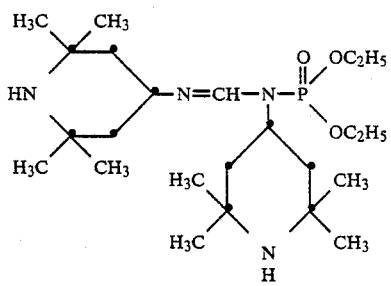

of melting point 104°–106° C.

Analysis for $C_{23}H_{47}N_4O_3P$ monohydrate: Calculated: C 57.7%; H 10.4%; N 11.7%; Found: C 57.37%; H 10.37%; N 11.6%.

EXAMPLE 51

Following the procedure of Example 4, and using the appropriate reagents, the compound of the formula

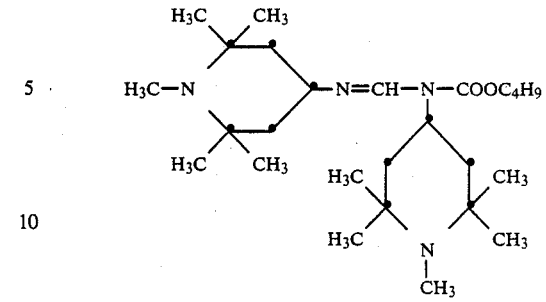

is prepared.

Boiling point: 186°–188° C. at 0.067 mbar.

As mentioned at the outset, the compounds of the formula (I) are very effective in improving the light stability, heat stability and oxidation stability of organic materials, preferably synthetic polymers, in particular polyolefins.

Examples of organic materials which can be stabilized with compounds of formula (I) are:

Polymers of monoolefins and diolefins, for example polyethylene (which may be crosslinked), polypropylene, polyisobutylene, poly-1-butene, polymethyl-1-pentene, polyisoprene or polybutadiene, and also polymers of cycloolefins, for example of cyclopentene or norbornene. Mixtures of the said polymers, for example mixtures of polypropylene with polyisobutylene.

Copolymers of monoolefins and diolefins with one another or with other vinyl monomers, for example ethylene/propylene, propylene/1-butene, propylene/isobutylene, ethylene/1-butene, propylene/butadiene, isobutylene/isoprene, ethylene/vinyl acetate, ethylene/alkyl acrylates, ethylene/alkyl methacrylates or ethylene/acrylic acid copolymers and their salts (ionomers) and terpolymers of ethylene with propylene and a diene such as hexadiene, dicyclopentadiene or ethylidenenorbornene.

Polystyrene and poly-(p-methylstyrene).

Copolymers of styrene or α-methylstyrene with dienes or acrylic derivatives, for example styrene/butadiene, styrene/acrylonitrile, styrene/ethyl methacrylate, styrene/butadiene/ethyl acrylate, styrene/acrylonitrile/methyl acrylate, high-impact strength mixtures of styrene copolymers and other polymers, for example a polyacrylate, a diene polymer or an ethylene/propylene/diene terpolymer, and block copolymers of styrene, for example styrene/butadiene/styrene, styrene/isoprene/styrene, styrene/ethylene/butylene/styrene or styrene/ethylene/propylene/styrene.

Graft copolymers of styrene, for example styrene of polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, and also mixtures with the copolymers mentioned under the preceding heading, for example the mixtures known as ABS, MBS, ASA or AES polymers.

Halogen-containing polymers, such as polychloroprene, chlorinated rubbers, chlorinated or sulfochlorinated polyethylene, polymers and copolymers of epichlorohydrin, polymers of halogen-containing vinyl compounds, for example polyvinyl chloride, polyvinylidene chloride, polyvinyl fluoride and polyvinylidene fluoride, and also copolymers thereof, for example vinyl chloride/vinylidene chloride, vinyl chloride/vinyl acetate or vinylidene chloride/vinyl acetate copolymers.

Polymers derived from α,β-unsaturated acids and their derivatives, such as polyacrylates and polymethacrylates, polyacrylamides and polyacrylonitrile.

Copolymers of the monomers under the preceding heading, mixed with one another or with other unsaturated monomers, for example acrylonitrile/butadiene, acrylonitrile/alkyl acrylate, acryl-o-nitrile/alkoxyalkyl acrylate or acrylonitrile/vinyl halide copolymers or acrylonitrile/alkyl methacrylate/butadiene terpolymers.

Polymers derived from unsaturated alcohols and amines or their acyl or acetal derivatives, such as polyvinyl alcohol, polyvinyl acetate, polyvinyl stearate, polyvinyl benzoate, polyvinyl maleate, polyvinyl butyral, polyallyl phthalate or polyallylmelamine.

Homopolymers and copolymers of cyclic ethers, such as polyalkylene glycols, polyethylene oxide, polypropylene oxide or their copolymers with bis-glycidyl ethers.

Polyacetals, such as polyoxymethylene and the polyoxymethylenes containing ethylene oxide as a comonomer.

Polyphenylene oxides and sulfides, and mixtures of polyphenylene oxides with polystyrene.

Polyurethanes derived on the one hand from polyethers, polyesters or polybutadiene with hydroxyl end groups and, on the other hand, aliphatic or aromatic polyisocyanates, and also their precursors (polyisocyanates, polyols or prepolymers). Polyamides and copolyamides derived from diamines and dicarboxylic acids and/or aminocarboxylic acids or the corresponding lactams, such as nylon-4, nylon-6, nylon-6/6, nylon-6/10, nylon-11, nylon-12, poly-2,4,4-trimethylhexamethylene-terephthalamide or poly-m-phenyleneisophthalamide, and also their copolymers with polyethers, for example with polyethylene glycols, polypropylene glycols or polytetramethylene glycols.

Polyureas, polyimides and polyamide-imides.

Polyesters derived from dicarboxylic acids and diols and/or hydroxycarboxylic acids or corresponding lactones, such as polyethylene terephthalate, polybutylene terephthalate, poly-1,4-dimethylolcyclohexane terephthalate, poly-2,2-(4-hydroxyphenyl)-propane terephthalate and polyhydroxybenzoate, and also the block copolyetheresters derived from polyethers with hydroxyl end groups.

Polycarbonates and polyesater-carbonates.

Polysulfones, polyether-sulfones and polyetherketones.

Crosslinked polymers derived from aldehydes on the one hand and phenols, ureas and melamines on the other hand, such as phenol/formaldehyde resins, urea/formaldehyde resins and melamine/formaldehyde resins.

Drying and non-drying alkyd resins.

Unsaturated polyester resins derived from copolyesters of saturated and unsaturated dicarboxylic acids with polyalcohols and vinyl compounds as crosslinking agents, and also their halogen-containing modifications of low inflammability.

Thermosetting acrylic resins derived from substituted acrylic esters, such as epoxy-acrylates, urethane-acrylates and polyester-acrylates.

Alkyd resins, polyester resins or acrylate resins mixed with melamine resins, urea resins, polyisocyanates or epoxide resins as crosslinking agents.

Crosslinked epoxide resins derived from polyepoxides, for example from bis-glycidyl ethers or cycloaliphatic diepoxides.

Natural polymers of the type of cellulose, rubber, gelatine and their derivatives with chemical polymer-homologous modifications, such as cellulose acetates, cellulose propionates and cellulose butyrates, or cellulose ethers such as methylcellulose.

Mixtures of the above polymers, for example PP/EPDM, nylon-6/EPDM or ABS, PVC/EVA, PVC/ABS, PVC/MBS, PC/ABS and PBTP/ABS.

The compounds of formula (I) are in particular useful in stabilizing polyethylen and polypropylen.

The compounds of the formula (I) can be mixed with the organic material in various proportions depending on the nature of the polymer, on the end use and on the presence of other additives.

In general, it is advantageous to employ from 0.01 to 5% by weight of the compounds of the formula (I), relative to the weight of the organic material, preferably from 0.05 to 1%.

The compounds of the formula (I) can be incorporated into the polymeric materials via various processes, such as dry blending in the form of powders, or wet mixing in the form of solutions or suspensions, or mixing in the form of a master-batch; in these operations, the polymer can be employed in the form of powder, granules, a solution, a suspension or in the form of a latex.

The polymers stabilized with the products of the formula (I) can be used for the preparation of moulded articles, films, tapes, fibres, monofilaments, surface-coatings and the like.

If desired, the stabilized compositions of this invention may optionally also contain for example from about 0.05 to about 5%, preferably from about 0.1 to about 2.5% by weight of various conventional additives, such as antioxidants, UV absorbers, nickel stabilizers, pigments, fillers, plasticizers, antistatic agents, flameproofing agents, lubricants, anti-corrosion agents, metal deactivators and others.

Examples of additives which can be mixed with the compounds of the formula (I) are in particular;

Antioxidants belonging to the following classes:

Alkylated monophenols, for example:

2,6-Di-t-butyl-4-methylphenol, 2-t-butyl-4,6-dimethylphenol, 2,6-di-t-butyl-4-ethylphenol, 2,6-di-t-butyl-4-n-butylphenol, 2,6-di-t-butyl-4-i-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol and 2,6-di-t-butyl-4-methoxymethylphenol.

Alkylated hydroquinones, for example:

2,6-Di-t-butyl-4-methoxyphenol, 2,5-di-t-butylhydroquinone, 2,5-di-t-amylhydroquinone and 2,6-diphenyl-4-octadecyloxyphenol.

Thiobisphenols, for example:

2,2'-Thio-bis-(6-t-butyl-4-methylphenol), 2,2'-thio-bis-(4-octylphenol), 4,4'-thio-bis-(6-t-butyl-3-methylphenol) and 4,4'-thio-bis-(6-t-butyl-2-methylphenol).

Alkylidene-bisphenols, for example:

2,2'-Methylene-bis-(6-t-butyl-4-methylphenol), 2,2'-methylene-bis-(6-t-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-[6-(α-methylbenzyl)-4-nonylphenol], 2,2'-methylene-bis-[6-(α,α-dimethylbenzyl)-4-nonylphenol], 2,2'-methylene-bis-(4,6-di-t-butylphenol), 2,2'-ethylidene-bis-(4,6-di-t-butylphenol), 2,2'-ethylidene-bis-(6-t-butyl-4-isobutylphenol), 4,4'-methylene-bis-(2,6-di-t-butylphenol), 4,4'-methylene-bis-(6-t-butyl-2-methylphenol), 1,1-bis-(5-t-butyl-4-hydroxy-2-methylphenyl)-butane, 2,6-bis-(3-t-butyl-5-methyl-2-hydroxybenzyl)-4-methylpenol, 1,1,3-tris-(5-t-butyl-4-hydroxy-2-methylphenyl)-butane, 1,1-bis-(5-t-butyl-4-hydroxy-2-methylphenyl)-3-n-dodecylmercaptobutane, ethylene glycol bis-[3,3-bis-(3'-t-butyl-4'-hydroxyphenyl-butyrate], bis-(3-t-butyl-4-hydroxy-5-methylphenyl)-dicyclopentadiene and bis-[2-(3'-t-butyl-2'-hydroxy-5'-methylbenzyl)-6-t-butyl-4-methylphenyl]terephthalate.

Benzyl compounds, for example:
1,3,5-Tris-(3,5-di-t-butyl-4-hydroxybenzyl)-2,4,6-trimethylbenzene, bis-(3,5-di-t-butyl-4-hydroxybenzyl)-sulfide, isooctyl 3,5-di-t-butyl-4-hydroxybenzyl-mercaptoacetate, bis-(4-t-butyl-3-hydroxy-2,6-dimethylbenzyl)dithiolterephthalate, 1,3,5-tris-(3,5-di-t-butyl-4-hydroxybenzyl)isocyanurate, 1,3,5-tris-(4-t-butyl-3-hydroxy-2,6-dimethylbenzyl)isocyanurate, dioctadecyl 3,5-di-t-butyl-4-hydroxybenzyl-phosphonate and calcium monoethyl 3,5-di-t-butyl-4-hydroxybenzyl-phosphonate.

Acylaminophenols, for example:
Lauric acid 4-hydroxyanilide, stearic acid 4-hydroxyanilide, 2,4-bis-(octylmercapto)-6-(3,5-t-butyl-4-hydroxyanilino)-s-triazine and octyl N-(3,5-di-t-butyl-4-hydroxyphenyl)-carbamate.

Esters of β-(3,5-di-t-butyl-4-hydroxyphenyl)-propionic acid with monohydric or polyhydric alcohols, for example:
Methanol, octadecanol, 1,6-hexanediol, neopentyl glycol, thiodiethylene glycol, diethylene glycol, triethylene glycol, pentaerythritol, tris-(hydroxyethyl)-isocyanurate and N,N'-bis-(hydroxyethyl)-oxamide.

Esters of β-(5-t-butyl-4-hydroxy-3-methylphenyl)-propionic acid with monohydric or polyhydric alcohols, for example:
Methanol, octadecanol, 1,6-hexanediol, neopentyl glycol, thiodiethylene glycol, diethylene glycol, triethylene glycol, pentaerythritol, tris-(hydroxyethyl)-isocyanurate and N,N'-bis-(hydroxyethyl)-oxamide.

Amides of β-(3,5-di-t-butyl-4-hydroxyphenyl)-propionic acid:
N,N'-Bis-(3,5-di-t-butyl-4-hydroxyphenylpropionyl)-hexamethylenediamine, N,N'-bis-(3,5-di-t-butyl-4-hydroxyphenylpropionyl)-trimethylenediamine and N,N'-bis-(3,5-di-t-butyl-4-hydroxyphenylpropionyl)-hydrazine.

UV absorbers and light stabilizers belonging to the following groups:

2-(2'-Hydroxyphenyl)-benzotriazoles, for example the 5'-methyl, 3',5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-sec.-butyl-5'-t-butyl, 4'-octoxy-3',5'-di-t-amyl and 3',5'-bis-(α,α-dimethylbenzyl) derivatives.

2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

Esters of various substituted benzoic acids, for example:
Phenyl salicylate, 4-t-butylphenyl salicylate, octylphenyl salicylate, dibenzoylresorcinol, bis-(4-t-butylbenzoyl)-resorcinol, benzoylresorcinol, 2,4-di-t-butylphenyl 3,5-di-t-butyl-4-hydroxybenzoate, hexadecyl 3,5-di-t-butyl-4-hydroxybenzoate and N-ethyl-N-phenyl-N'-(p-ethoxycarbonylphenyl)-formamidine.

Acrylates, for example:
Ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

Nickel compounds, for example:
Nickel complexes of 2,2'-thio-bis-[4-(1,1,3,3-tetramethylbutyl)-phenol], such as the 1:1 or 1:2 complexes, which may contain additional ligands such as n-butylamine, triethanolamine or N-cyclohexyl-diethanolamine, nickel dibutyldithiocarbamate, nickel salts of the monoalkyl esters of 4-hydroxy-3,5-di-t-butylbenzylphosphonic acid, such as the methyl, ethyl or butyl esters, nickel complexes of ketoximes such as 2-hydroxy-4-methylphenyl undecyl ketoxime and nickel complexes of 1-phenyl-4-lauroyl-5-hydroxypyrazole with or without additional ligands.

Sterically hindered amines, for example:
Bis-(2,2,6,6-tetramethylpiperidyl)sebacate, bis-(1,2,2,6,6-pentamethylpiperidyl)sebacate,bis-(1,2,2,6,6-pentamethylpiperidyl) n-butyl-3,5-di-t-butyl-4-hydroxybenzylmalonate, the condensation product of 1-(hydroxyethyl)-2,2,6,6-tetramethyl-4-hydroxypiperidine and succinic acid, the condensation product of N,N'-bis-(2,2,6,6-tetramethylpiperidyl)hexamethylenediamine and 4-t-octylamino-2,6-dichloro-1,3,5-triazine, tris-(2,2,6,6-teramethylpiperidyl)nitrilotriacetate, tetrakis(2,2,6,6-tetramethylpiperidyl) 1,2,3,4-butanetetracarboxylate and 1,1'-(1,2-ethanediyl)-bis-(3,3,5,5-tetramethylpiperazinone).

Oxalic acid diamides, for example:
4,4'-Dioctyloxy-oxanilide, 2,2'-dioctyloxy-5,5'-di-t-butyloxanilide, 2,2'-didodecyloxy-5,5'-di-t-butyloxanilide, 2-ethoxy-2'-ethyloxanilide, N,N'-bis-(3-dimethylaminopropyl)-oxalamide, 2-ethoxy-5-t-butyl-2'-ethyloxanilide and its mixtures with 2-ethoxy-2'-ethyl-5,4'-di-t-butyloxanilide, and mixtures of ortho- and para-methoxy- and also o- and p-ethoxy-di-substituted oxanilides.

Metal deactivators, for example:
N,N'-diphenyloxamide, N-salicylal-N'-salicyloylhydrazine, N,N'-bis-(salicyloyl)-hydrazine, N,N'-bis-(3,5-di-t-butyl-4-hydroxyphenylpropionyl)-hydrazine, 3-salicyloylamino-1,2,4-triazole and bis-(benzylidene)-oxalodihydrazide.

Phosphites and phosphonites, for example:
Triphenyl phosphite,diphenyl alkyl phosphites, phenyl dialkyl phosphites, tris-(nonylphenyl)phosphite, trilauryl phosphite, trioctadecyl phosphite, distearyl pentaerythritol diphosphite, tris-(2,4-di-t-butylphenyl)-phosphite, diisodecyl pentaerythritol diphosphite, di-(2,4-di-t-butylphenyl)pentaerythritol diphosphite, tristearyl sorbitol diphosphite and tetrakis-(2,4-di-t-butyl-phenyl) 4,4'-diphenylene-diphosphonite.

Peroxide-destroying compounds, for example:
Esters of β-thiodipropionic acid, for example the lauryl, stearyl, myristyl or tridecyl esters, mercaptobenzimidazole or the zinc salt of 2-mercaptobenzimidazole, zinc dibutyl-dithiocarbamate, dioctadecyl disulfide and pentaerythritol tetrakis-(β-dodecyl-mercapto)propionate.

Polyamide stabilizers, for example:

Copper salts in combination with iodides and/or phosphorus compounds and divalent manganese salts.

Basic costabilizers, for example:

Melamine, polyvinylpyrrolidone, dicyandiamide, triallyl cyanurate, urea derivatives, hydrazine derivatives, amines, polyamides, polyurethanes, alkali metal or alkaline earth metal salts of higher fatty acids, for example calcium stearate, zinc stearate, magnesium stearate, sodium ricinoleate and potassium palmitate, antimony pyrocatecholate or zinc pyrocatecholate.

Nucleating agents, for example:

4-T-butylbenzoic acid, adipic acid and diphenylacetic acid.

Fillers and reinforcing agents, for example:

Calcium carbonate, silicates, glass fibres, asbestos, talc, kaolin, mica, barium sulfate, metal oxides and hydroxides, carbon black and graphite.

Further additives, for example:

Plasticizers, lubricants, emulsifiers, pigments, fluorescent brighteners, flameproofing agents, antistatic agents and foaming agents.

The efficiency, as stabilizers, of the products prepared according to the invention, is illustrated in the examples which follow, in which some products obtained in the preparation examples are used for stabilizing polypropylene plates and tapes.

EXAMPLE 52

1 g of each of the compounds indicated in Table 1, 0.5 g of tris-(2,4-di-t-butylphenyl)phosphite, 0.5 g of pentaerythritol tetrakis-[3-(3,5-di-t-butyl-4-hydroxyphenyl)-propionate], 1 g of Blue Phthalocyanine, 1 g of calcium stearate and 1,000 g of polypropylene powder (melt index=2.4 g/10 min; measured at 230° C. and 2,16 kp) are intimately mixed in a slow mixer. The mixtures obtained are extruded at a temperature of 200°–220° C. to give polymer granules which are then converted into plaques of 2 mm thickness by injection-moulding at 190°–220° C.

The plaques obtained are exposed in a model 65 WR Weather-O-Meter (ASTM G26-77) at a black panel temperature of 63° C. until the start of superficial embrittlement (chalking).

For comparison, a polypropylene plaque prepared under the same conditions as indicated above, but without the addition of the compounds of the invention, is exposed.

Table 1 shows the exposure time (in hours) required to reach the start of superficial embrittlement.

TABLE 1

| Stabilizer | Embrittlement time (hours) |
|---|---|
| Without stabilizer | 500 |
| Compound of Example 4 | 4,300 |
| Compound of Example 5 | 4,800 |
| Compound of Example 6 | 4,000 |
| Compound of Example 8 | 3,600 |
| Compound of Example 13 | 3,800 |
| Compound of Example 21 | 3,750 |
| Compound of Example 49 | 3,900 |

EXAMPLE 53

1 g of each of the compounds indicated in Table 2, 0.5 g of tris-(2,4-di-t-butylphenyl)phosphite, 0.5 g of pentaerythritol tetrakis-[3-(3,5-di-t-butyl-4-hydroxyphenyl)-propionate] and 1 g of calcium stearate are mixed in a slow mixer with 1,000 g of polypropylene powder (melt index=3 g/10 min; measured at 230° C. and 2.16 kp).

The mixtures obtained are extruded at a temperature of 200°–220° C. to give polymer granules which are then converted into stretched tapes of 50 μm thickness and 2.5 mm width, using a semitechnical-scale apparatus (Leonard, Sumisago (VA)-Italy), under the following working conditions:

Extruder temperature: 220°–240° C.

Head temperature: 260° C.

Stretch ratio: 1:6

The tapes thus prepared are exposed, mounted on a white card, in a model 65 WR Weather-O-Meter (ASTM G26-77), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

For comparison, tapes prepared under the same conditions as indicated above, but without the addition of the compounds of the invention, are exposed. The results obtained are shown in Table 2.

TABLE 2

| Stabilizer | $T_{50}$ (hours) |
|---|---|
| Without stabilizer | 190 |
| Compound of Example 10 | 2,710 |
| Compound of Example 13 | 2,150 |
| Compound of Example 14 | 2,500 |
| Compound of Example 18 | 2,200 |
| Compound of Example 20 | 2,100 |
| Compound of Example 21 | 2,400 |
| Compound of Example 33 | 2,800 |
| Compound of Example 34 | 3,150 |
| Compound of Example 46 | 2,450 |
| Compound of Example 49 | 2,300 |

What is claimed is:

1. A compound of formula I

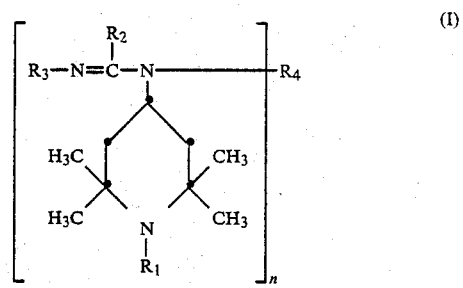

in which $R_1$ is hydrogen, O·, CN, NO, cyanomethyl, $C_1$–$C_{12}$-alkyl, $C_3$–$C_{12}$-alkenyl or $C_3$–$C_{12}$-alkynyl subject to the proviso that the carbon atom attached to the nitrogen atom is a primary carbon atom, $C_7$–$C_{12}$-aralkyl, $C_1$–$C_{12}$-alkanoyl, $C_3$–$C_{12}$-alkenoyl, $C_3$–$C_{12}$-alkynoyl, benzoyl or benzoyl substituted by one or more of $C_1$–$C_4$-alkyl or —OH 2,3-epoxypropyl, OH-monosubstituted $C_2$–$C_6$-alkyl or 2,3-dihydroxypropyl, $R_2$ is hydrogen, $C_1$–$C_{18}$-alkyl, $C_5$–$C_{18}$-cycloalkyl, $C_6$–$C_{18}$-aryl or $C_7$–$C_{18}$-aralkyl, $R_3$ is $C_6$–$C_{18}$-aryl or a group of the formula (II)

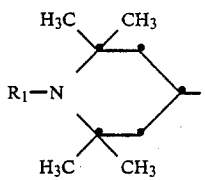

in which
R$_1$ is as defined above,
n is an integer from 1 to 3, and
R$_4$ is a triazinyl radical of a valency equal to n, with the proviso that when n is 1, R$_4$ is

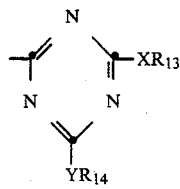

where R$_{13}$ and R$_{14}$ are independently C$_1$-C$_{18}$-alkyl, C$_2$-C$_6$-alkyl substituted by OH, by C$_1$-C$_{18}$-alkoxy or by C$_2$-C$_{18}$-dialkylamino; C$_5$-C$_{18}$-cycloalkyl, C$_3$-C$_{18}$-alkenyl, C$_6$-C$_{18}$-aryl, C$_7$-C$_{18}$-aralkyl or a group of formula II, or R$_{13}$ and R$_{14}$ are hydrogen, and
X and Y are independently a direct bond, —O— or

where R$_{16}$ is hydrogen, C$_1$-C$_{18}$-alkyl, C$_5$-C$_{18}$-cycloalkyl, C$_3$-C$_{18}$-alkenyl, C$_6$-C$_{18}$-aryl, C$_7$-C$_{18}$-aralkyl or a group of formula II, or R$_{16}$ is OH-monosubstituted C$_2$-C$_6$-alkyl, or the groups R$_{13}$X and R$_{14}$Y are independently 1-pyrrolidinyl, 1-piperidyl or 4-methyl-1-piperazinyl,
when n is 2, R$_4$ is

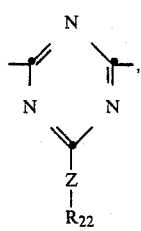

where
R$_{22}$ is as defined for R$_{13}$ and R$_{14}$,
Z is as defined for X and Y, or —ZR$_{22}$ is 1-pyrrolidinyl, 1-piperidyl, 4-methyl-1-piperazinyl or halogen, and
when n is 3, R$_4$ is a 1,3,5-triazine-2,4,6-triyl group.

2. A compound according to claim 1, in which R$_1$ is hydrogen, methyl, allyl, benzyl or acetyl, R$_2$ is hydrogen, C$_1$-C$_{12}$-alkyl, C$_6$-C$_9$-cycloalkyl or C$_6$-C$_9$-aryl, R$_3$ is C$_6$-C$_{12}$-aryl or a group of the formula (II), n is 1, 2 or 3 and, if n is 1, R$_4$ is

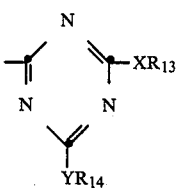

in which
R$_{13}$ and R$_{14}$, which are identical or different, are hydrogen, C$_1$-C$_{12}$-alkyl, C$_6$-C$_9$-cycloalkyl, allyl or a group of the formula (II), X and Y, which are identical or different, are —O— or $\diagdown$N—R$_{16}$,
$\diagup$ where R$_{16}$ is hydrogen, C$_1$-C$_{12}$-alkyl, C$_6$-C$_9$-cycloalkyl, allyl or a group of the formula (II), or the groups R$_{13}$X— and R$_{14}$Y— or which are identical or different, are a 1-pyrrolidinyl, 1-piperidyl, group or, if n is 2, R$_4$ is in which
R$_{22}$ is hydrogen, C$_1$-C$_{12}$-alkyl, C$_6$-C$_9$-cycloalkyl, allyl or a group of the formula (II) and Z is —O— or $\diagdown$N—R$_{16}$
$\diagup$ with R$_{16}$ as defined hereinabove, or, if n is 3, R$_4$ is a 1,3,5-triazine-2,4,6-triyl group.

3. A compound according to claim 1, in which R$_1$ is hydrogen or methyl, R$_2$ is hydrogen or methyl, R$_3$ is 2,2,6,6-tetramethyl-4-piperidyl or 1,2,2,6,6-pentamethyl-4-piperidyl, n is 1, 2 or 3 and, if n is 1, R$_4$ is in which
R$_{13}$ and R$_{14}$, which are identical or different, are C$_1$-C$_{12}$-alkyl, cyclohexyl, allyl or a group of the formula (II) with R$_1$ being hydrogen or methyl, and X and Y, which are identical or different, are a group

where
R$_{16}$ is hydrogen, C$_1$-C$_{12}$-alkyl, cyclohexyl, allyl or a group of the formula (II) with R$_1$ being hydrogen or methyl and, if n is 2, R$_4$ is

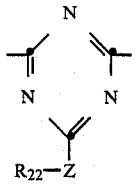

in which
R$_{17}$ is C$_4$-C$_{10}$-alkylene, C$_6$-C$_8$-cycloalkylene or a group of C$_6$-C$_{13}$-arylene, R$_{22}$ is C$_1$-C$_{12}$-alkyl, cyclohexyl, allyl or a group of the formula (II) with R$_1$ being hydrogen or methyl, and Z is —O— or

with R$_{16}$ being as defined hereinabove, and, if n is 3, R$_4$ is a 1,3,5-triazine-2,4,6-triyl group.

4. A compound according to claim 1 wherein R$_1$ is hydrogen, C$_1$-C$_4$-alkyl allyl, benzyl or acetyl.

5. A compound according to claim 1 wherein R$_2$ is hydrogen, C$_1$-C$_4$-alkyl, cyclohexyl, phenyl or benzyl and R$_3$ is phenyl unsubstituted or substituted by C$_2$-C$_4$-alkoxycarbonyl or is a group of the formula (II) in which R$_1$ is as defined in claim 1.

6. A compound according to claim 1 wherein R$_1$ is hydrogen or methyl, R$_2$ is hydrogen or C$_1$-C$_4$-alkyl and R$_3$ is phenyl substituted by C$_2$-C$_4$-alkoxycarbonyl or is a group of formula (II) in which R$_1$ is as defined hereinabove.

7. A compound according to claim 1 wherein n is 1 or 2.

8. A compound according to claim 7 wherein n is 1.

9. A compound according to claim 7 wherein n is 2.

10. A compound according to claim 1 wherein n is 1, 2 or 3 and if n=1, R$_4$ is

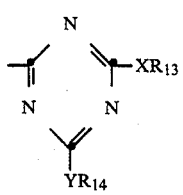

wherein
R$_{13}$ and R$_{14}$ are independently hydrogen, C$_1$-C$_8$-alkyl, allyl or a group of formula (II) wherein R$_1$ is as defined in claim 1, X and Y are independently —O— or

R$_{16}$ is hydrogen, C$_1$-C$_8$-alkyl, OH—mono-substituted C$_2$-C$_4$-alkyl, allyl or a group of the formula (II) wherein R$_1$ is as defined in claim 1, if n=2, R$_4$ is

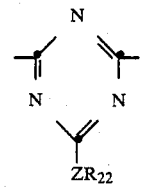

and wherein
R$_{22}$ is C$_1$-C$_8$-alkyl, OH-monosubstituted C$_2$-C$_4$-alkyl or allyl, Z is —O— or

with R$_{16}$ being as defined hereinabove or —ZR$_{22}$ is halogen, and, if n=3, R$_4$ is 1,3,5-triazine-2,4,6-triyl.

11. A compound according to claim 1 wherein R$_1$ is hydrogen, R$_2$ is hydrogen or methyl, R$_3$ is 2,2,6,6-tetramethyl-4-piperidyl, n is 1, 2 or 3 and, if n is 1, R$_4$ is

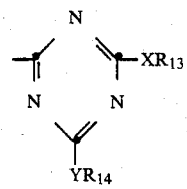

in which
R$_{13}$ and R$_{14}$ are independently C$_1$-C$_8$-alkyl or allyl, X and Y are independently —O— or

with R$_{16}$ being hydrogen, C$_1$-C$_8$-alkyl, allyl or 2,2,6,6-tetramethyl-4-piperidyl and, if n is 2, R$_4$ is

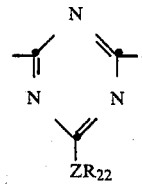

in which
R$_{22}$ is C$_1$-C$_8$-alkyl or allyl and Z is —O— or

with $R_{16}$ being as defined hereinabove and, if n is 3, $R_4$ is a 1,3,5-triazine-2,4,6-triyl group.

12. A compound according to claim 1, in which $R_1$ is hydrogen, $R_2$ is hydrogen or methyl, $R_3$ is 2,2,6,6-tetramethyl-4-piperidyl, n is 1 or 2 and, if n is 1, $R_4$ is

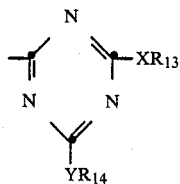

in which
$R_{13}$ and $R_{14}$ are independently $C_1$-$C_4$-alkyl, X and Y are

with $R_{16}$ being 2,2,6,6-tetramethyl-4-piperidyl and, if n is 2, $R_4$ is

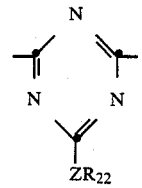

in which
$R_{22}$ is $C_1$-$C_4$-alkyl or allyl and Z is —O— or

with $R_{16}$ being hydrogen, $C_1$-$C_4$-alkyl or allyl.

13. The compound

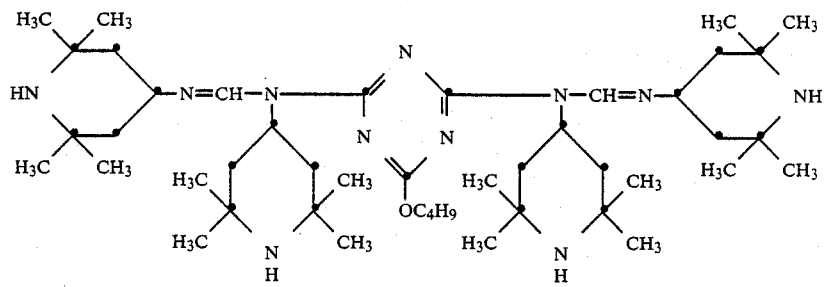

or

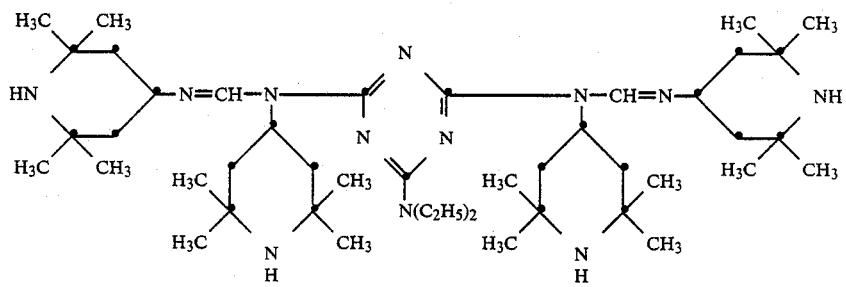

according to claim 1.

14. A composition of matter comprising a synthetic polymer subject to oxidative, thermal or light induced degradation stabilized with an effective stabilizing amount of a compound of claim 1.

15. A composition according to claim 14, wherein the organic material is a polyolefin.

16. A composition according to claim 15, wherein the polyolefin is polyethylene or polypropylene.

17. A composition according to claim 14, which, in addition to the compound of formula (I), also comprises other conventional additives for synthetic polymers.

18. A method for stabilizing a synthetic polymer against oxidative, thermal or light induced degradation which comprises
incorporating into said synthetic polymer an effective stabilizing amount of a compound according to claim 1.

* * * * *